(12) United States Patent
Buckland et al.

(10) Patent No.: US 12,080,404 B2
(45) Date of Patent: Sep. 3, 2024

(54) METHODS, SYSTEMS AND COMPUTER PROGRAM PRODUCTS FOR RETROSPECTIVE DATA MINING

(71) Applicant: Translational Imaging Innovations, Inc., Hickory, NC (US)

(72) Inventors: Eric L. Buckland, Hickory, NC (US); Joseph Carroll, New Berlin, WI (US); Robert C. Williams, Durham, NC (US); Andrew J. Witchger, Jr., Durham, NC (US)

(73) Assignee: Translational Imaging Innovations, Inc., Hickory, NC (US)

( * ) Notice: Subject to any disclaimer, the term of this patent is extended or adjusted under 35 U.S.C. 154(b) by 562 days.

(21) Appl. No.: 16/839,475

(22) Filed: Apr. 3, 2020

(65) Prior Publication Data

US 2021/0193297 A1 Jun. 24, 2021
US 2022/0148710 A9 May 12, 2022

Related U.S. Application Data

(63) Continuation-in-part of application No. PCT/US2019/049472, filed on Sep. 4, 2019.
(Continued)

(51) Int. Cl.
*G16H 30/20* (2018.01)
*G06F 9/54* (2006.01)
(Continued)

(52) U.S. Cl.
CPC ............ *G16H 30/20* (2018.01); *G06F 9/542* (2013.01); *G06F 11/3476* (2013.01);
(Continued)

(58) Field of Classification Search
CPC ..... G16H 30/20; G06F 9/542; G06F 11/3476; G06F 21/6218; G06F 2221/2141; G06T 7/20
See application file for complete search history.

(56) References Cited

U.S. PATENT DOCUMENTS 5,867,602 A  2/1999 Zandi et al.
5,999,911 A  12/1999 Berg et al.
(Continued)

FOREIGN PATENT DOCUMENTS

CN  106682530 A  5/2017
JP  2018133080 A  8/2018
(Continued)

OTHER PUBLICATIONS

International Search Report and Written Opinion of the International Searching Authority for PCT/US2021/024834, mailed Jul. 15, 2021, 10 pages.
(Continued)

*Primary Examiner* — Saleh Najjar
*Assistant Examiner* — Devin E Almeida
(74) *Attorney, Agent, or Firm* — Stanek Lemon Crouse & Meeks, PA

(57) ABSTRACT

Integrated systems for collecting, storing, and distribution of images acquired of subjects in a research or clinical environment are provided. The system includes an image and data repository including a plurality of images originating from one or more image-generating devices, data associated with the images, and data associated with imaged subjects; and a workflow management module in direct communication with the image and data repository and with the one or more image-generating devices and/or storage devices that store the images of the imaged subjects, the workflow management module being configured to transport the
(Continued)

images directly from the one or more image-generating devices and/or storage devices to the image and data repository and to manage the collation and distribution of images, data associated with the raw images and the data associated with the imaged subjects in the image and data repository. The workflow management module includes a data integration module, a data management module, a pre-processing engine and a data utilization module.

20 Claims, 19 Drawing Sheets

Related U.S. Application Data

(60) Provisional application No. 62/829,790, filed on Apr. 5, 2019, provisional application No. 62/829,797, filed on Apr. 5, 2019, provisional application No. 62/727,072, filed on Sep. 5, 2018.

(51) Int. Cl.
*G06F 11/34* (2006.01)
*G06F 21/62* (2013.01)
*G06T 7/20* (2017.01)

(52) U.S. Cl.
CPC ............ *G06F 21/6218* (2013.01); *G06T 7/20* (2013.01); *G06F 2221/2141* (2013.01)

(56) References Cited

U.S. PATENT DOCUMENTS

| | | | |
|---|---|---|---|
| 6,058,215 A | 5/2000 | Schwartz et al. | |
| 6,891,973 B1 | 5/2005 | Atsumi et al. | |
| 6,904,161 B1 | 6/2005 | Becker et al. | |
| 6,937,767 B1 | 8/2005 | Burak et al. | |
| 6,996,549 B2 | 2/2006 | Zhang et al. | |
| 7,024,046 B2 | 4/2006 | Dekel et al. | |
| 7,218,789 B2 | 5/2007 | Faber et al. | |
| 7,471,850 B2 | 12/2008 | Srinivasan | |
| 7,519,591 B2 | 4/2009 | Landi et al. | |
| 8,583,466 B2 | 11/2013 | Margulies et al. | |
| 8,682,910 B2 | 3/2014 | Fu et al. | |
| 8,694,646 B1 | 4/2014 | Kothari et al. | |
| 8,867,807 B1 | 10/2014 | Fram | |
| 8,879,813 B1 | 11/2014 | Solanki et al. | |
| 9,135,320 B2 | 9/2015 | Goyal et al. | |
| 9,147,179 B2 | 9/2015 | Syeda-Mahmood et al. | |
| 9,324,022 B2 | 4/2016 | Williams, Jr. et al. | |
| 9,355,273 B2 | 5/2016 | Stevens et al. | |
| 9,395,959 B2 | 7/2016 | Hatfield et al. | |
| 9,589,374 B1 | 3/2017 | Gao et al. | |
| 9,635,000 B1 | 4/2017 | Muftic | |
| 9,760,807 B2 | 9/2017 | Zhou et al. | |
| 9,767,307 B2* | 9/2017 | Cismas ............... G06F 21/6218 |
| 9,846,938 B2 | 12/2017 | Steigauf et al. | |
| 10,140,421 B1* | 11/2018 | Bernard ................. G06N 3/084 |
| 10,515,126 B2* | 12/2019 | Kurian .................... G06F 16/93 |
| 2004/0122790 A1* | 6/2004 | Walker ..................... G16H 30/40 |
| 2006/0285730 A1 | 12/2006 | Habets et al. | |
| 2007/0067252 A1 | 3/2007 | Hengerer | |
| 2009/0171708 A1 | 7/2009 | Bobak et al. | |
| 2010/0049740 A1 | 2/2010 | Iwase et al. | |
| 2010/0070306 A1 | 3/2010 | Dvorak et al. | |
| 2010/0174558 A1 | 7/2010 | Smith et al. | |
| 2010/0241990 A1 | 9/2010 | Gabriel et al. | |
| 2011/0110568 A1 | 5/2011 | Vesper et al. | |
| 2013/0144678 A1 | 6/2013 | Ramachandran | |
| 2013/0208955 A1 | 8/2013 | Zhao et al. | |
| 2013/0208966 A1 | 8/2013 | Zhao et al. | |
| 2014/0142984 A1* | 5/2014 | Wright ................ G06F 21/6245 |
| | | | 705/3 |
| 2014/0153808 A1* | 6/2014 | Wu ...................... G06Q 10/103 |
| | | | 382/131 |
| 2014/0350954 A1 | 11/2014 | Ellis et al. | |
| 2015/0149208 A1 | 5/2015 | Lynch et al. | |
| 2015/0332283 A1 | 11/2015 | Witchey | |
| 2016/0092721 A1* | 3/2016 | Kanagasingam ......... G06T 7/10 |
| | | | 348/78 |
| 2016/0330027 A1 | 11/2016 | Ebrahimi | |
| 2017/0076043 A1* | 3/2017 | Dormer .................. G16H 40/67 |
| 2017/0147296 A1 | 5/2017 | Kumar et al. | |
| 2017/0231594 A1 | 8/2017 | Dominick | |
| 2017/0300627 A1* | 10/2017 | Giordano ............ G06F 21/6245 |
| 2018/0046766 A1 | 2/2018 | Deonarine et al. | |
| 2018/0068438 A1 | 3/2018 | DeVries | |
| 2018/0121620 A1 | 5/2018 | Bastide et al. | |
| 2019/0080207 A1 | 3/2019 | Chang | |
| 2021/0193297 A1* | 6/2021 | Buckland ............... G16H 40/20 |
| 2022/0076802 A1* | 3/2022 | Bondar .................. G16H 50/70 |

FOREIGN PATENT DOCUMENTS

| | | |
|---|---|---|
| RU | 2 256 224 C1 | 10/2005 |
| WO | WO 2018/069736 A1 | 4/2018 |

OTHER PUBLICATIONS

Abràmoff, M. D., Lavin, P. T., Birch, M., Shah, N. & Folk, J. C. Pivotal trial of an autonomous AI-based diagnostic system for detection of diabetic retinopathy in primary care offices, *npj Digit. Med.* 1, 39 (2018).
Bach et al., "Data Anonymization patent landscape," CRORR 8 (2017, pp. 265-281).
Brainard, D. H., Cooper, R. F., Morgan, J. I. W., Tuten, W. S. & Dubra, A. Non-invasive assessment of human cone photoreceptor function: erratum. *Biomed. Opt. Express* 9, 1842 (2018).
Broadgate, S., Yu, J., Downes, S. M. & Halford, S. Unravelling the genetics of inherited retinal dystrophies: Past, present and future. *Prog, Retin, Eye Res.* 59, 53-96 (2017).
Carroll, J. et al. Effects of Intraframe Distortion on Measures of Cone Mosaic Geometry from Adaptive Optics Scanning Light Ophthalmoscopy. *Transl. Vis. Sci. Technol.* 5, 10 (2016).
CDC Vision Health Initiative Economic Studies. https://www.cdc.gov/visionhealth/projects/economic_studies.htm (2017).
Cooper, R. F. et al. Automatic detection of cone photoreceptors in split detector adaptive optics scanning light ophthalmoscope images. *Biomed. Opt. Express* 7, 2036 (2016).
Cooper, R. F., Wilk, M. A., Tarima, S. & Carroll, J. Evaluating descriptive metrics of the human cone mosaic. *Investig. Ophthalmol. Vis. Sci.* 57, 2992-3001 (2016).
Cremers, F. P. M., Boon, C. J. F., Bujakowska, K. & Zeitz, C. Special issue introduction: Inherited retinal disease: Novel candidate genes, genotype-phenotype correlations, and inheritance models. *Genes (Basel)* 9, 1-10 (2018).
Cunefare, D. et al. Deep learning based detection of cone photoreceptors with multimodal adaptive optics scanning light ophthalmoscope images of achromatopsia. *Biomed. Opt. Express* 9, 3740 (2018).
Cunefare, D. et al. Open source software for automatic detection of cone photoreceptors in adaptive optics ophthalmoscopy using convolutional neural networks. *Sci. Rep.* 7, 1-11 (2017).
DiCarlo, J. E., Mahajan, V. B. & Tsang, S. H. Gene therapy and genome surgery in the retina. *J. Clin. Invest.* 128, 2177-2188 (2018).
FDA. *Medical Device Development Tools (MDDT)*, (2019).
Gasparini, S. J., Llonch, S., Borsch, O. & Ader, M. Transplantation of photoreceptors into the degenerative retina: Current state and future perspectives. *Prog. Retin. Eye Res.* 1-37 (2018) doi:10.1016/j.preteyeres.2018.11.001.
Godara, P., Dubis, A. M., Roorda, A., Duncan, J. L. & Carroll, J. Adaptive optics retinal imaging: Emerging clinical applications. in *Optometry and Vision Science* 87, 930-941 (2010).
Hunter, J. J., Cookson, C. J., Kisilak, M. L., Bueno, J. M. & Campbell, M. C. W. Characterizing image quality in a scanning laser ophthalmoscope with differing pinholes and induced scattered light. *J. Opt. Soc. Am. A. Opt. Image Sci. Vis.* 24, 1284-95 (2007).

(56) References Cited

OTHER PUBLICATIONS

Kaluzny, J. et al. Hyperspectral measurement of retinal oximetry in diabetes. *Investig. Ophthalmol. Vis. Sci.* 57(12), 3743 (2016).
Kaplan, Bonnie, "Selling Health Data: De-Identification, Privacy and Speech," ISPS—Bioethics Working Paper, Oct. 7, 2017, 33 pages.
Langlo, C. S. et al. An Automated Reference Frame Selection (ARFS) Algorithm for Cone Imaging with Adaptive Optics Scanning Light Ophthalmoscopy. *Transl. Vis. Sci. Technol.* 6, 9 (2017).
Litts, K. M., Cooper, R. F., Duncan, J. L. & Carroll, J. Photoreceptor-Based Biomarkers in AOSLO Retinal Imaging. *Invest. Ophthalmol. Vis. Sci.* 58, BIO255-BIO267 (2017).
Mantha, S., Roizen, M. F., Fleisher, L. A., Thisted, R. & Foss, J. Comparing methods of clinical measurement: Reporting standards for bland and altman analysis. *Anesth. Analg.* 90, 593-602 (2000).
Martin Bland, J. & Altman, D. Statistical Methods for Assessing Agreement Between Two Methods of Clinical Measurement. *Lancet* 327, 307-310 (1986).
Notification of International Search Report and Written Opinion of the International Searching Authority, PCT/US2019/049472, Nov. 7, 2019, 18 pages.
Office Action, U.S. Appl. No. 13/668,509, filed Apr. 4, 2018, 22 pages.
Ourselin, S. et al. Automatic Cone Photoreceptor Localisation in Healthy and Stargardt Afflicted Retinas Using Deep Learning. *Sci. Rep.* 8. 1-13 (2018).
Pardue, M. T. & Allen, R. S. Neuroprotective strategies for retinal disease. *Prog. Retin. Eye Res.* 65, 50-76 (2018).
Park YR, Yoon YJ, Koo H, Yoo S, Choi CM, Beck SH, Kim TW. Utilization of a Clinical Trial Management System for the Whole Clinical Trial Process as an Integrated Database: System Development. J Med Internet Res. Apr. 24, 2018;20(4):e103. doi: 10.2196/jmir.9312.PMID: 29691212; PMCID: PMC5941091.
Pennington, K. L. & DeAngelis, M. M. Epidemiology of age-related macular degeneration (AMD): associations with cardiovascular disease phenotypes and lipid factors. *Eye Vis.* 3, 1-20 (2016).
Russell, S. et al. Efficacy and safety of voretigene neparvovec (AAV2-hRPE65v2) in patients with RPE65-mediated inherited retinal dystrophy: a randomised, controlled, open-label, phase 3 trial. *Lancet* 390, 849-860 (2017).
Scoles, D. et al. In Vivo Imaging of Human Cone Photoreceptor Inner Segments. *Investig. Ophthalmol. Vis. Sci.* 55, 4244-4251 (2014).
Stein, D. M. et al. A new quality assessment parameter for optical coherence tomography. *Br. J. Ophthalmol.* 90, 186 LP-190 (2006).
Sugita, S. et al. Stemming retinal regeneration with pluripotent stem cells. *Prog. Retin. Eye Res.* 0-1 (2018). doi:10.1016/j.preteyeres. 2018.11.003 Russell, S. et al. Efficacy and safety of voretigene neparvovec (AAV2-hRPE65v2) in patients with RPE65-mediated inherited retinal dystrophy: a randomised, controlled, open-label, phase 3 trial. *Lancet* 390, 849-860 (2017).
Takahashi, V. K. L., Takluti, J. T., Jauregui, R. & Tsang, S. H. Gene therapy in inherited retinal degenerative diseases, a review. *Ophthalmic Genet.* 39, 560-568 (2018).
Talcott, K. E. et al. Longitudinal study of cone photoreceptors during retinal degeneration and in response to ciliary neurotrophic factor treatment. *Investig. Ophthalmol. Vis. Sci.* 52, 2219-2226 (2011).
Wahle et al., "Extending the XNAT archive tool for image and analysis management in ophthalmology research," Proceedings of SPIE, vol. 8674, Mar. 29, 2013, 16 pages.

* cited by examiner

METHODS, SYSTEMS AND COMPUTER PROGRAM PRODUCTS FOR RETROSPECTIVE DATA MINING

CLAIM OF PRIORITY

The present application is a continuation-in-part of PCT Application Serial No. PCT/US19/49472, filed on Sep. 5, 2019 entitled Methods, Systems and Computer Program Products for Retrospective Data Mining, which claims priority to U.S. Provisional Application No. 62/727,072, filed Sep. 5, 2018, entitled Methods, Systems and Computer Program Products for Retrospective Data Mining and claims priority to U.S. Provisional Application Nos. 62/829,790 and 62/829,797, both filed on Apr. 5, 2019, the contents of which are hereby incorporated herein by reference as if set forth in their entirety.

STATEMENT OF GOVERNMENT SUPPORT

This inventive concept was made with government support under Contract No. 1R43EY030408 awarded by the National Institutes of Health and the National Eye Institute. The Government has certain rights in this invention.

BACKGROUND

Images play an increasingly important role in the diagnosis, treatment, and management of disease. In particular, the way images are used in the diagnosis and management of disease is rapidly evolving. At the most basic level, images are presented to experts for interpretation. Such is often the case with radiograms, sonograms, and photographs. The experts may be, for example, point of care physicians, radiologists, pathologists, and trained technical experts. Increasingly, quantitative analysis is applied to individual images and the quantitative information may be directly interpreted, compared to normative data, or compared to trending data. In such cases, the diagnostic conclusion and impact on treatment remains in the hands of the expert care giver. Big Data and methods of artificial intelligence (AI) are increasingly important to the discovery of diagnostic markers, or imaging biomarkers. The process for developing, validating, and deploying new diagnostic markers for clinical care or as outcome measures in clinical trials for new treatments require an end to end framework for collection, management, and operation on increasingly large volumes of images and data.

SUMMARY

Some embodiments of the present inventive concept provide integrated systems for collecting, storing, and distribution of images acquired of subjects in a research or clinical environment. The system includes an image and data repository including a plurality of images originating from one or more image-generating devices, data associated with the images, and data associated with imaged subjects; and a workflow management module in direct communication with the image and data repository and with the one or more image-generating devices and/or storage devices that store the images of the imaged subjects, the workflow management module being configured to transport the images directly from the one or more image-generating devices and/or storage devices to the image and data repository and to manage the collation and distribution of images, data associated with the raw images and the data associated with the imaged subjects in the image and data repository. The workflow management module includes a data integration module, a data management module, a pre-processing engine and a data utilization module. The data integration module receives data from one or more user-selected electronic data sources in connection with the workflow management module; the data management module parses the data received through the data integration module into records within the image and data repository; the pre-processing engine is configured to run one or more automated algorithms on images and data prior to storing images or data in the repository; and the data utilization module distributes images and data from the repository to authorized users for analysis according to automation rules defined within the workflow management module. The automation rules include rules for masking of data for human annotation, labelling and grading and rules for parsing data into grading sets, algorithm training sets, algorithm testing sets, and algorithm validation sets. The workflow management module further includes automated logging to record and trace activities associated with automated processing routines applied to images and data within the framework of the workflow management module in communication with the image and data repository and automated logging to user access records for all images and data within the framework of the workflow management module in communication with the image and data repository. The ordered combination of processes and automations include a specific workflow are configured by the user using a library of available operations.

In further embodiments, the workflow management module may further include a data analysis module configured to communicate with a plurality of libraries, each of the plurality of libraries being directed to metadata that travels with the images and data, ownership and permissions associated with images and data, and automation processes that apply to classes of images and data.

In still further embodiments, the plurality of libraries may be constantly updated with new libraries and sub-libraries based on evolving exams and details thereof performed in a research or clinical environment.

In some embodiments, the data analysis module may include a plurality of separate modules directed to image and data cleaning, annotation and grading; automated image and data analysis; and analysis methods and biomarker development and validation.

In further embodiments, the data analysis module may be configured to analyze a collection of available images and/or data provided through a data utilization module according to a recipe, wherein the recipe is configured to segregate, mask, and allocate data according to a library of rules assigned to a protocol; assemble data into a trackable collection and allocate the data for review.

In still further embodiments, the system may further include a mobile device that communicates with modules in the system, the mobile device configured to track a subject through a series of one or more image or data-generating exams; record relevant information and results during the exam; transfer the recorded information and results from the mobile device to the data analysis module and/or a storage repository, and provide a notification to one or more users that an exam has been completed and the images and data have been transferred.

In some embodiments, the pre-processing engine may be further configured to receive the images, data associated with the images, and data associated with imaged subjects through the workflow management module; determine a specific set of instructions associated with the received images, data associated with the images, and data associated with imaged subjects from the workflow management module; and process the received images, data associated with the images, and data associated with imaged subjects based on the specific set of instructions associated with the received images and data from the workflow management module; store the processed images and data with traceability to the input images and data log the operations applied to the images and data.

In further embodiments, the specific set of instructions associated with the received images, data associated with the images, and data associated with imaged subjects may be determined by an indicator set in a data field, the indicator directing the pre-processing engine to the specific set of instructions for the received raw images, data associated with the raw images, and data associated with imaged subjects from a particular data-generating device.

In still further embodiments, the pre-processing engine may be further configured to at least one of validate, quantify, annotate and classify the raw images, data associated with the raw images, and data associated with imaged subjects received from the workflow management module.

In some embodiments, the pre-processing engine may be configured to remove non-essential or private data from the raw images, data associated with the raw images, and data associated with imaged subjects; store the removed non-essential or private data; and before recycling the non-essential or private data, request permission from a user associated with the raw images and data.

In further embodiments, the workflow management module may store the images, data associated with the images, and data associated with imaged subjects in a structured manner using a relational or structured query language (SQL) database and wherein the cloud storage module stores the de-identified, processed images and data in an unstructured manner using a non-relational or Non-SQL database.

In still further embodiments, the system may further include at least one of the following modules in the cloud an algorithm module in communication with the cloud storage module, the algorithm module configured to apply a set of rules to at least a portion of the de-identified, processed images and data stored in the cloud storage module; a recipe module in communicate with the cloud storage module, the recipe module configured to apply a series of algorithms to at least a portion of de-identified, processed images and data stored in the cloud storage module; and a derivation module in communication with the cloud storage module, the derivation module configured to use at least a portion of the de-identified, processed images and data stored in the cloud storage module and derive new images and data therefrom.

In some embodiments, the derivation module may be configured to assess quality of the de-identified, processed images and data; reduce noise in de-identified, processed images and data; segment the images and data; and/or measure de-identified, processed images and data.

In further embodiments, de-identified, processed images and data stored in the cloud storage module may be automatically updated by various modules in the cloud.

In still further embodiments, the modules in the cloud may utilize one or more of artificial intelligence (AI), statistical abstraction; image abstraction and image extraction.

In some embodiments, the de-identified, processed images and data stored in the cloud storage module may include at least one of statistical data; processed images; reduced images; retrospective images; in vivo images; in vitro images; functional test results; and biospecimen test results.

In further embodiments, transactions and operations may be applied to the raw images, data associated with the raw images, and data associated with imaged subjects and to subsequent processed images and data resulting from the transactions and operations are recorded in a blockchain-like ledger.

In still further embodiments, the transactions and operations recorded in the ledger may include allocation of subsets of images and data used for training, testing, and validation operations.

Related methods and computer program products are also provided.

DETAILED DESCRIPTION OF EMBODIMENTS

Figure 1:
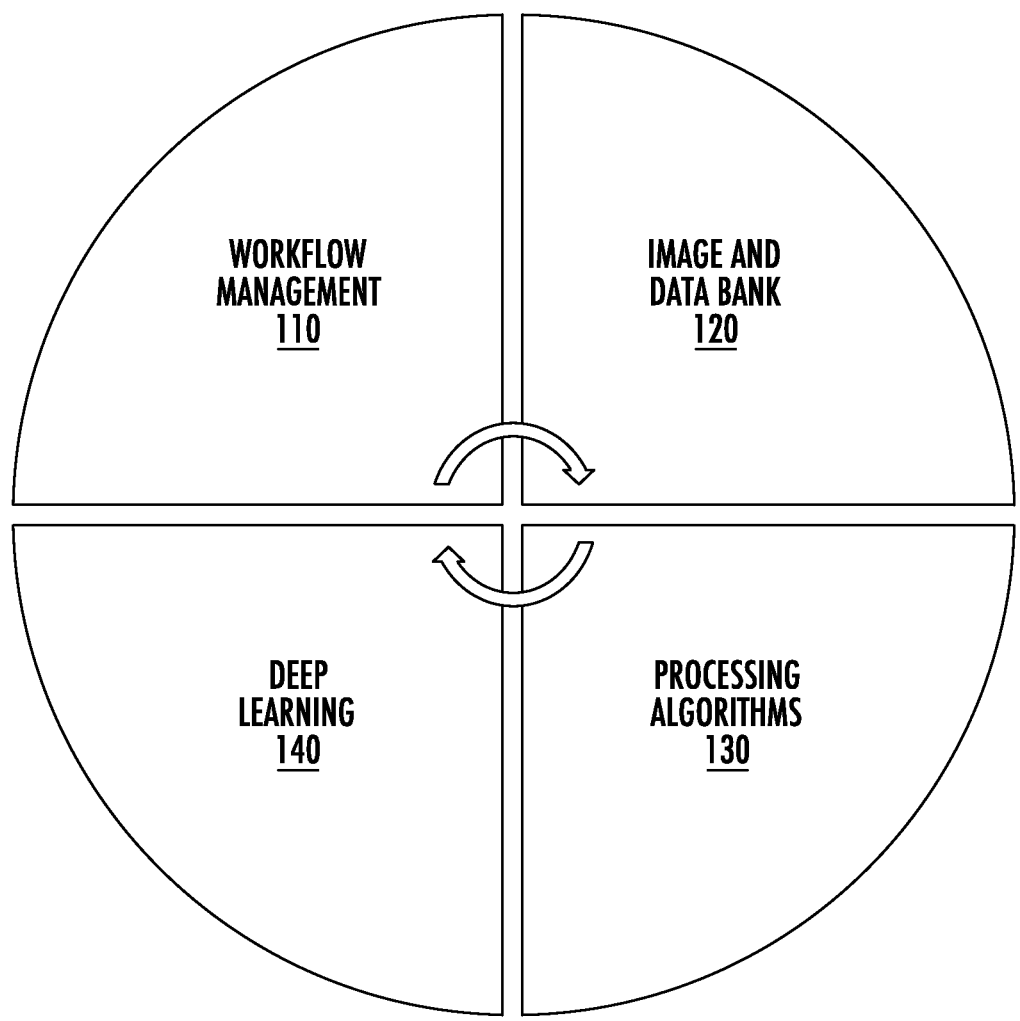
FIG. 1 is diagram illustrating components of an example deep learning system in accordance with some embodiments of the present inventive concept.

The inventive concept now will be described more fully hereinafter with reference to the accompanying drawings, in which illustrative embodiments of the inventive concept are shown. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

As will be appreciated by one of skill in the art, the inventive concept may be embodied as a method, data processing system, or computer program product. Accordingly, the present inventive concept may take the form of an entirely hardware embodiment or an embodiment combining software and hardware aspects all generally referred to herein as a "circuit" or "module." Furthermore, the present inventive concept may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present inventive concept may be written in an object-oriented programming language such as Java®, Smalltalk or C++. However, the computer program code for carrying out operations of the present inventive concept may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The inventive concept is described in part below with reference to a flowchart illustration and/or block diagrams of methods, systems and computer program products according to embodiments of the inventive concept. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

As discussed in the background, images play an increasingly important role in the diagnosis and management of disease. With the advent of artificial intelligence (AI), machine learning and deep learning techniques, it is becoming viable to enrich the diagnostic content of images by training images against expertly graded examples. For example, a product that uses fundus photographs (photographs of the retina) to provide an automated diagnosis of diabetic retinopathy had been developed and approved by the Federal Drug Administration (FDA). This diagnosis application, which is based on images, highlights both the promise and the limitations of approaches to deep learning. First, the accuracy of the diagnosis is generally less than ninety percent and relegated to patients with intermediate to advanced grades of diabetic retinopathy. While an important contribution to the diagnostic regime, the technology is not ready for early prediction of disease or disease progression. Furthermore, the regulatory clearance related to this product is limited to images acquired using one model of one fundus camera from one manufacturer. So, while this application of deep learning is a sign of the future of AI in image-based medical diagnostics, improvements are desired.

The technology industry is providing very advanced systems and solutions to provide users access to cloud storage and computing facilities and to computational systems for deep learning. For example, cloud-based services are provided by Google, Amazon, Microsoft, international business machines (IBM) and the like. These services are making a rapid impact on the development of deep learning technologies across a variety of applications including medical applications.

Research and proofs of concept for deep learning are useful, but the target is translation of research to the clinic. This generally requires moving algorithms through rigorous regulatory processes. The FDA is demonstrating intention to support such digital advances. In order to successfully navigate the regulatory landscape, it remains very important to follow a structured, reproducible and validated design control process and to provide clear evidence for the verification and validation of digital medical solutions. This process starts early, with clear definition of the intended use for a new medical device, including a digital medical device, deriving requirements for the performance and deployment of the device consistent with the intended use, translating market requirements to technical specifications, developing the device, freezing developing, and completing verification and validation according the requirements and the intended use, respectively.

Critically, the verification and validation steps must be traceable to the requirements. In prognostic and diagnostic devices derived from medical images, the workflow for shepherding a new product through successful regulatory clearance is a very complex and cumbersome process involving the development of clinical trial protocols, management of patient consents and patient privacy, scheduling patients, and following formal protocols in the collection, storage and management of image data and associated metadata. In order to develop the diagnostic indicators, biomarkers, or endpoints, the research team will need to iterate through a number of steps.

Accordingly, some embodiments of the present inventive concept use a central application as a platform for prospective and retrospective image based biomedical research, in addition to an image bank of millions of images and image processing algorithms to increase the efficiency of imaging-driven biomedical research and clinical trials through structured workflow management; build and manage a de-identified image bank as a platform for the sharing and re-use of expensive research and clinical images; provide a platform for both the prospective and biomarkers, endpoints, and clinical trial outcome measures; provide a platform for third-party development of algorithms for image processing and deep learning; and increase the efficacy of translating these activities to the clinic and market by structuring these activities in a rigorous, transparent, reproducible and validated process.

LATTICE is an Electronic Research Record developed at the Medical College of Wisconsin to increase the efficiency of translational research in vision and ophthalmology. As implemented, the software has specific utility to retinal imaging. As an architecture, it is a flexible Software as a service (SaaS) platform for living-subjects image and data based translational research. LATTICE and its related functionality may be used in some embodiments of the present inventive concept and, therefore, these teachings are incorporated herein by reference as if set forth in their entirety.

LATTICE is a software system for managing the scheduling of subjects, tracking of subjects during research encounters, and collection of clinical images for running efficient prospective clinical trials in ophthalmology. This platform has significant potential for commercialization, as the trends in ophthalmology and translational medicine strongly favor efficiency in clinical trials, maximum re-use and sharing of images collected under federal grants, and rapid advancement of deep learning technologies that require banks of public health information (PHI) protected images to train and validate new diagnostic algorithms.

As discussed above and illustrated in FIG. 1, embodiments of the present inventive concept combine a workflow management system 110, for example, LATTICE; an image database (image and data bank) 120, for example, a library of approximately 3,000,000 or more retinal images; and processing algorithms 130 (modules that perform these algorithms), for example, as deployed within MOSAIC, which houses intelligent image quantification algorithms, developed with deep learning principals (AI) 140 to provide a commercial platform for managing image-based clinical trials, maximizing licensed re-use of images for retrospective studies, and developing learning algorithms for advancing clinical diagnostics. The integrated system in accordance with some embodiments of the present inventive concept is referred to herein as a Data and Workflow Management System (DWMS).

It will be understood that although the DWMS discussed herein is discussed with respect to LATTICE, MOSAIC and a specific database of retinal images, embodiments of the present inventive concept are not limited to this configuration. For example, any workflow management system, image bank or processing algorithms and associated modules may be used to provide the results as discussed herein without departing from the scope of the present inventive concept.

As used herein, "an image bank" can include any collection of images as needed for embodiments of the present inventive concept. For example, an image bank may include a collection of optical coherence tomography (OCT), OCTA photographic, and adaptive-optic images and associated metadata, collected under internal ratings-based (IRB) approval with informed consent allowing image re-use. As used herein, "metadata" refers to, but is not limited to, any patient demographics, medical histories, diagnoses that inform the images, subject to any and all protections under applicable United States and international patient privacy regulations. Metadata may also include any data that provides information about other data. In other words, it is "data about data." Many distinct types of metadata exist, including descriptive metadata, structural metadata, administrative metadata, reference metadata and statistical metadata. For example, in a database when information is added or deleted, these actions receive an invisible trail in the metadata. This metadata can be discovered and used to inform the visible data in the system.

As will be discussed further herein, the DWMS in accordance with embodiments of the present inventive concept use the workflow management system and image and data bank to create a unified platform for the collection, mining, sharing, and exploring of pre-clinical and clinical image data. The objective is to create a "Design Control" system for image-based research that maximizes the translation of research insights and new diagnostic modalities to the market to advance ocular healthcare and reduce healthcare costs.

Users of this product may include academic researchers, researchers in the biotech and pharma space developing new therapies, contract research organizations (CROs) running clinical trials on behalf of industrial partners, as well as the big data firms that are seeking to sell cloud services and establish their own footprint in healthcare. Embodiments of the present inventive concept may be configured to link to web tools for researchers to accelerate their own algorithm development, training, and testing.

Figure 2:
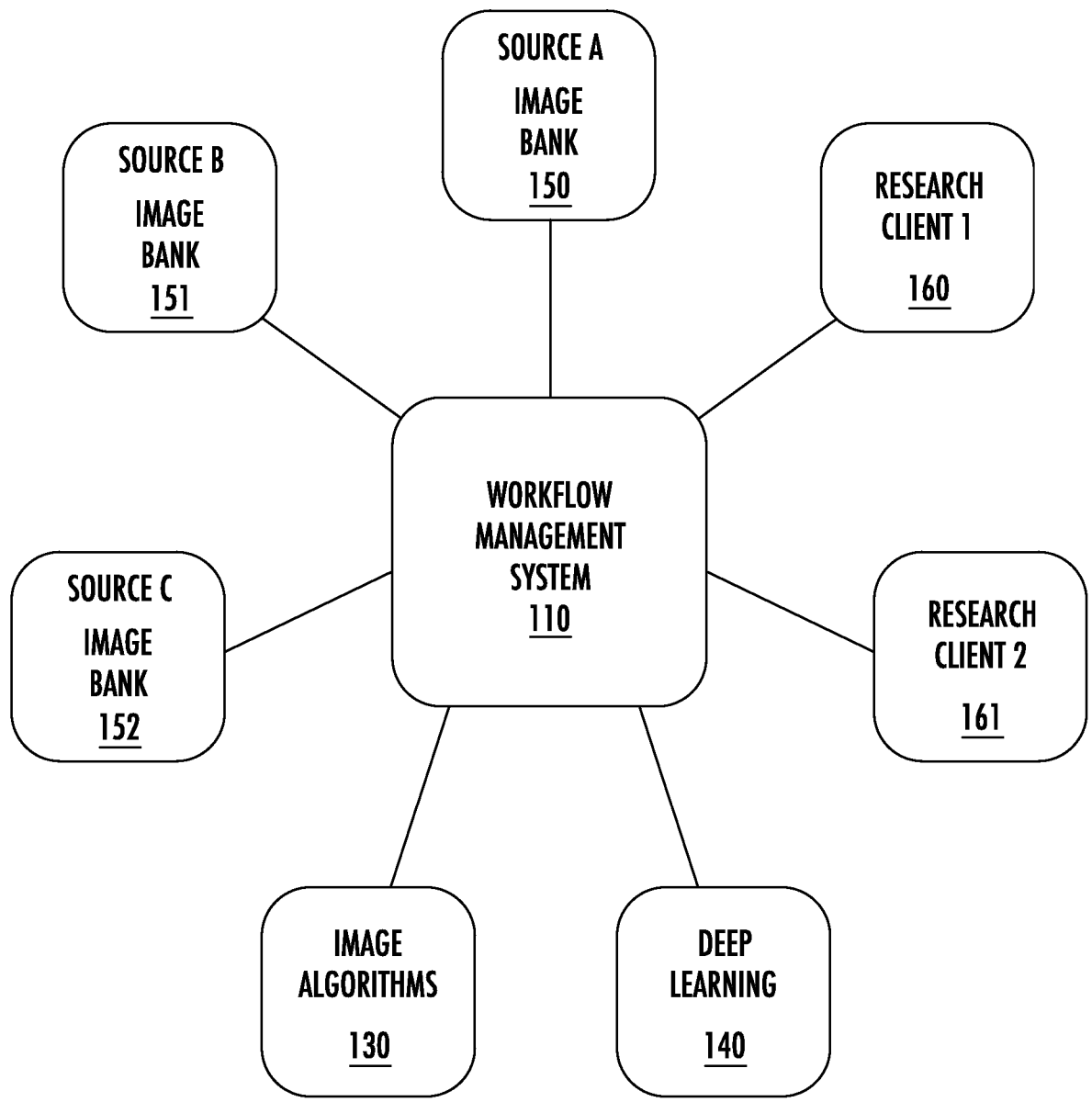
FIG. 2 is a block diagram of an integrated system in accordance with some embodiments of the present inventive concept.

The fully integrated platform in accordance with embodiments discussed herein will further be discussed with respect to FIG. 2. As illustrated therein, the platform includes a workflow management solution 110, for example, LATTICE, for collecting, managing and mining image-based research and clinical data. In some embodiments, subscription services for use of LATTICE or other solution may be provided. Some embodiments of the present inventive concept may expand image-centric fields beyond ophthalmology without departing from the scope of the present inventive concept. In other words, image banks including any type of image may be used in accordance with embodiments discussed herein. As illustrated FIG. 2, the workflow management function 110 couples multiple image banks, Source A 150, Source B 151 and Source C 152, multiple research clients 161 and 162, processing algorithms 130 and associated modules, for example, MOSAIC, and deep learning modules 140 to provide the integrated system.

In some embodiments, the image banks 120, 150, 151 and 152 may include a collection of approximately 3,000,000 images collected over a decade of research, or any other quantity of images and associated data collected over any period of time. As illustrated in FIG. 2, the workflow management system 110 can have access to more than one image bank, Source A 150, Source B 151 and Source C 152. In some embodiments, the image bank may be curated, categorized, anonymized, and validated for sharing and re-use with evidence of provenance, IRB approval, and patient consents that authorize retrospective use of images under defined circumstances.

Figure 3:
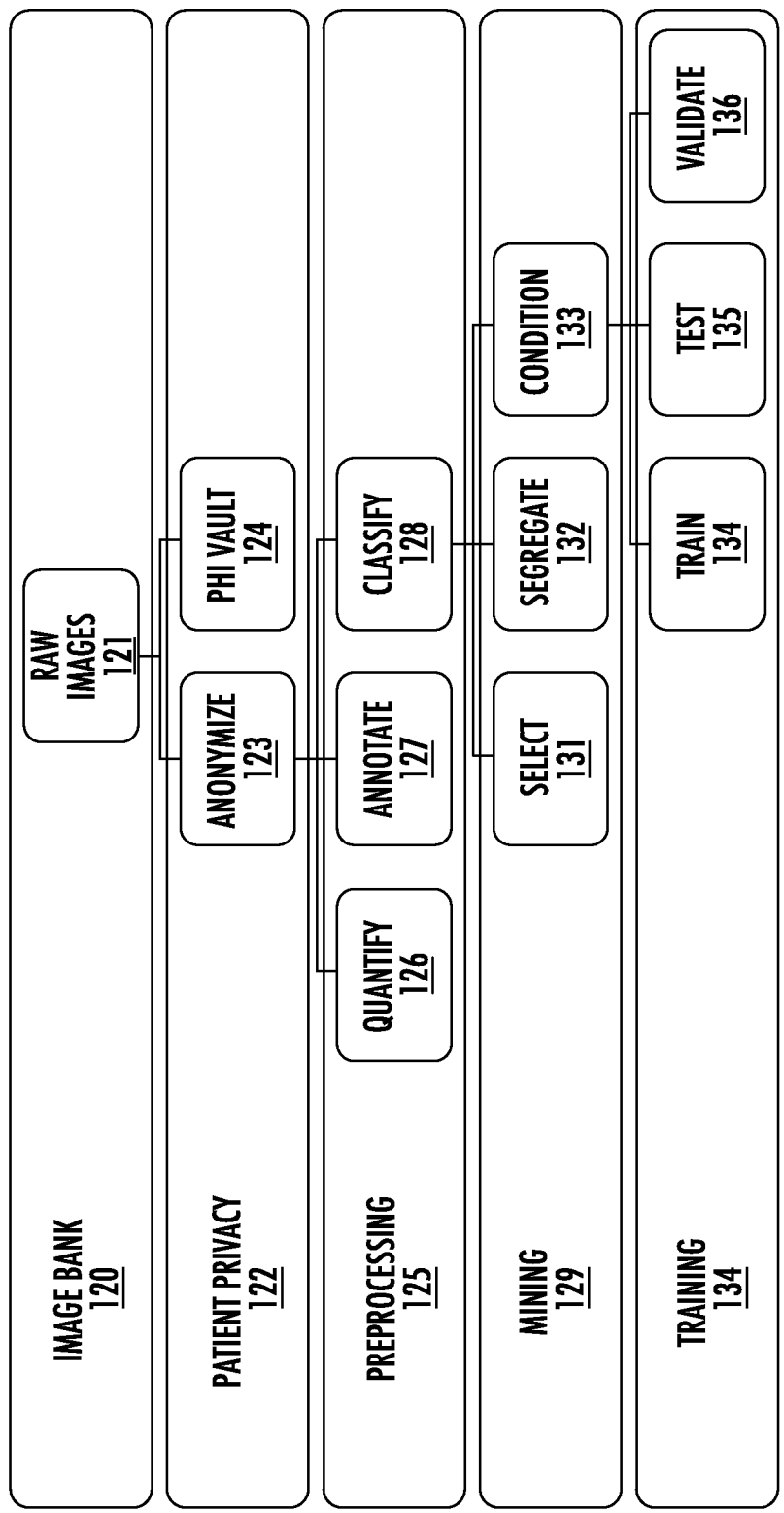
FIG. 3 is a diagram illustrating various categories of data according to some embodiments of the present inventive concept.

Referring now to FIG. 3, a diagram illustrating various categories of data according to some embodiments of the present inventive concept will be discussed. As illustrated, an image bank may include raw images 121, which may be processed to provide images compliant with patient privacy standards 122 (anonymize 123, Patient Health Information (PHI) vault 124); pre-processed 125 to allow annotation and the like (quantify 126, annotate 127 and classify 128); mined 129 to find specific images meeting specific criteria (select 131, segregate 132 and condition 133); and used in training 134, testing 135 and validation 136.

Providing the various processed images as discussed with respect to FIG. 3 may add value to the services. For example, pre-processing 125 the images may include manual, automated, or semi-automated marking, segmentation, and quantification 126. This may include layer segmentation, cell counting (as with MOSAIC) or other marking that reduce the raw image to a derived data set suitable for further analysis. Medical annotation 127 may involve the addition of expert opinion to the image, identifying pathology or disease, or grading disease according to standards. Classification 128 may involve establishing a schema for categorizing images for mining and retrospective analysis. In each case, the original raw images and data are preserved, and actions taken with respect to the images and data are recorded as transactions, and the results from transactions are stored as derived results that link back to the raw images and data and the processing transactions.

Some embodiments of the present inventive concept are provided for use in deep learning studies (AI). In these embodiments, images drawn from the image bank 120 may be further segregated into randomized independent sets for training 134, testing 135 and validation 136 of algorithms as illustrated in FIG. 3. These actions may be performed automatically in some embodiments of the present inventive concept. In order to increase the robustness of deep learning algorithms, training images 134 may be further conditioned to added representative real-world variability to the images. For example, some embodiments of the present inventive concept may provide automated variability to images for increasing training sets. The more the workflow can be standardized and reproduced, the more efficient the study. Additionally, the more standardized and reproducible the workflow, the easier to generate credible, reproducible results and the faster the regulatory clearance process for resultant clinical solutions. Thus, embodiments may provide shareable workflow protocols for reproducibility and verifiability.

MOSAIC houses a specific algorithm for analyzing photoreceptors in adaptive optic enhanced fundus images. Adaptive optic (AO) imaging systems are not yet a standard of care in ophthalmology, but are used in research and clinical trials. Broadening the analysis of AO images through MOSAIC in accordance with some embodiments of the present inventive concept may help to identify clinical endpoints that can drive adoption of adaptive optics and address open clinical questions related to inherited retinal disease and age-related degenerative disease. In some embodiments, MOSAIC may be appropriately applied to images in the image bank 120 to provide a reduced data set (locations and count of photoreceptors) for further analysis. Alternatively, MOSAIC may be applied to the image bank 120 to provide an annotation to the images as part of the ontology for categorizing images as will be discussed further herein. For example, images may be annotated according to an ontology (a set of concepts and categories in a subject area or domain that shows their properties and the relations between them) and automate extension of annotations based on additions to ontology.

Figure 4:
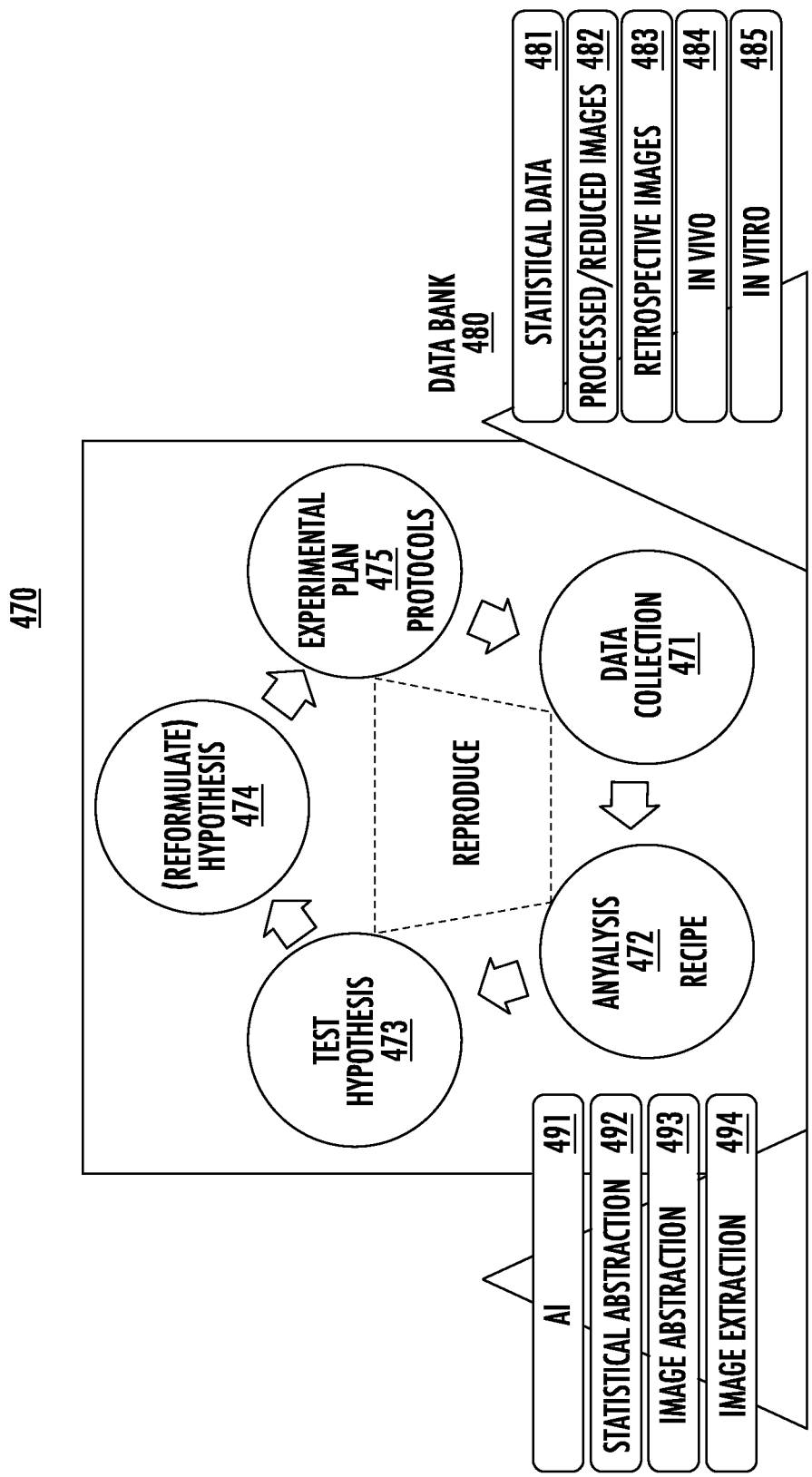
FIGS. 4 and 5 are diagrams of data flows in accordance with some embodiments of the present inventive concept.

As discussed above, embodiments of the present inventive concept provide an integrated system for multiple uses, for example, training, testing, validation, and diagnosis. FIG. 4 is a diagram illustrating the data flow in a test environment of how data is collected, analyzed and used to create and reformulate hypotheses in accordance with some embodiments of the present inventive concept. As illustrated in FIG. 4, the workflow 470 collects data 471 from the data bank 480 including, for example, statistical data 481, processed/reduced images 482, retrospective images 483, in vivo data 484, in vitro data 485 and the like. This data may be analyzed 472 using recipes. For example, in some embodiments, multi-step recipes may be automatically applied to data to create a series of stored and traceable intermediate steps and the recipes may be modified and rerun to provide differential results that are automatically organized.

Referring again to FIG. 4, analyzing 472 the data 480 may include deep learning 490 including AI 491, statistical abstraction 492, image abstraction 493, image extraction 493 and the like. Using this analysis, a hypothesis 473 may be generated, tested and reformulated 474. From this, an experimental plan 475 may be created using protocols and the like. As illustrated by the arrows in FIG. 4, these steps may be repeated over and over to constantly refine and redefine the results. Further and unique to embodiments of the present inventive concept, each step maintains complete traceability. In other words, from any step, the starting point (original image and/or data) may be found, thereby maintain providence of each piece of data—backwards and forwards.

As used herein, the term "recipes" refers to the various algorithms that may be applied by modules of the present inventive concept running on a processor to the raw data to provide new sets of data. For example, one "recipe" may be used to anonymize the data, i.e. remove all "metadata" that points to a specific patient to which the data refers. Other recipes may involve image processing, statistics and the like. Recipes may be user customizable and there are generally no limits to the number of recipes that can be created.

Figure 5:
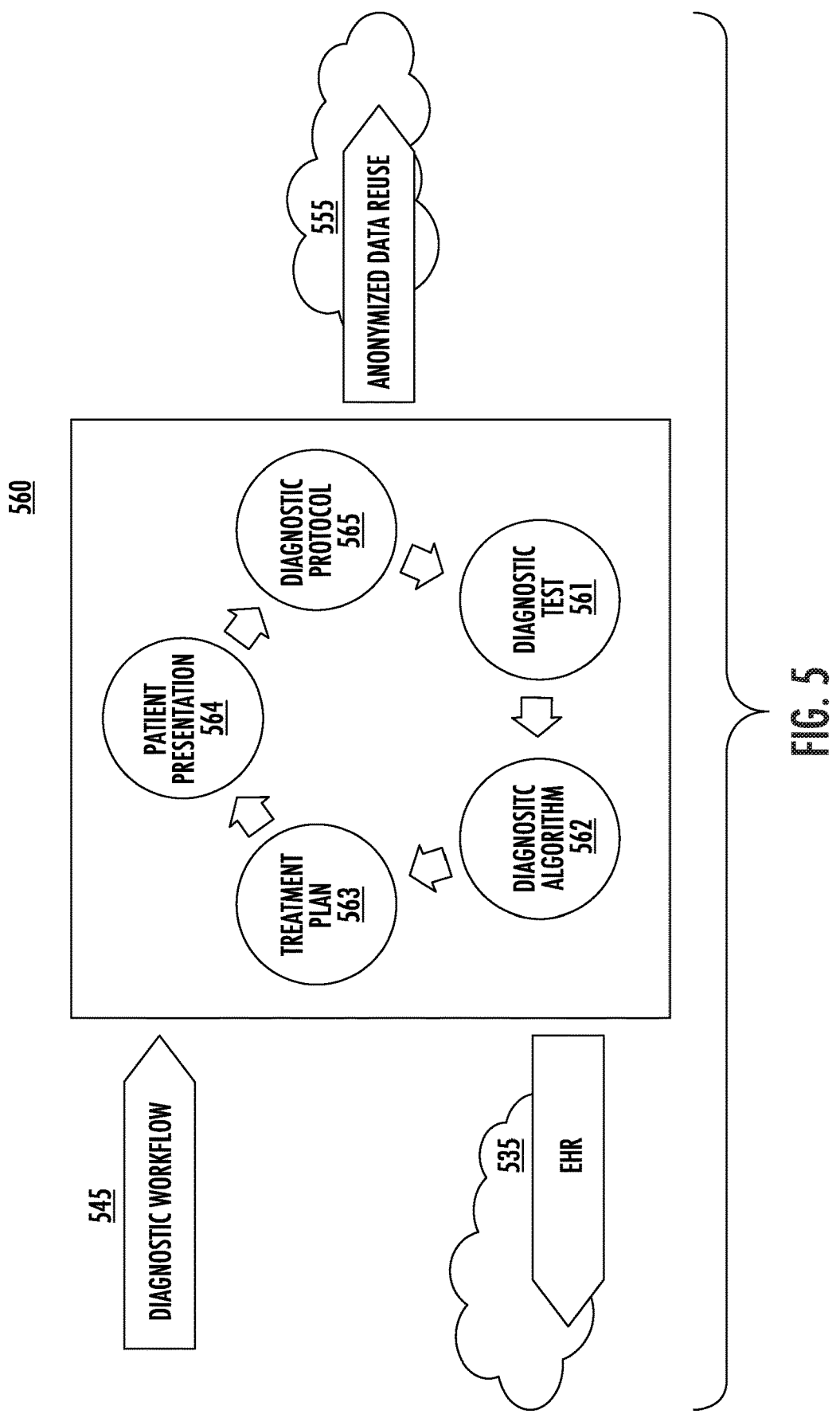

Referring now to FIG. 5, a block diagram illustrating a diagnostic workflow for a patient diagnosis in accordance with some embodiments of the present inventive concept will now be discussed. As illustrated, the diagnostic workflow 560 includes a diagnostic test module 561 which provides the initial data with respect to the patient. This data is submitted to the diagnostic algorithm 562. As discussed above, this algorithm may have access to historical data in a data bank in any form as well as various deep learning modules or other algorithmic recipes. The data may also be stored in an electronic health record (EHR) 535 or anonymized and stored for reuse 555 as discussed herein. Once the data has been run through the diagnostic algorithms 562, a treatment plan 563 may be created. Details of the patient's response to the treatment 564 may be observed and the diagnostic protocol 565 may be revised accordingly. Thus, some embodiments of the present inventive concept incorporating a response function module to measure the outcome of the treatment plan. Then the response function can be used to modify the treatment plan to produce a different or more favorable result.

As discussed above with respect to FIG. 4, the process may be repeated over and over to refine the results until a specialized treatment plan to which the patient responds is found. As further discussed above, each of these steps can be traced, both forward and backward without departing from the scope of the present inventive concept.

Figure 6:
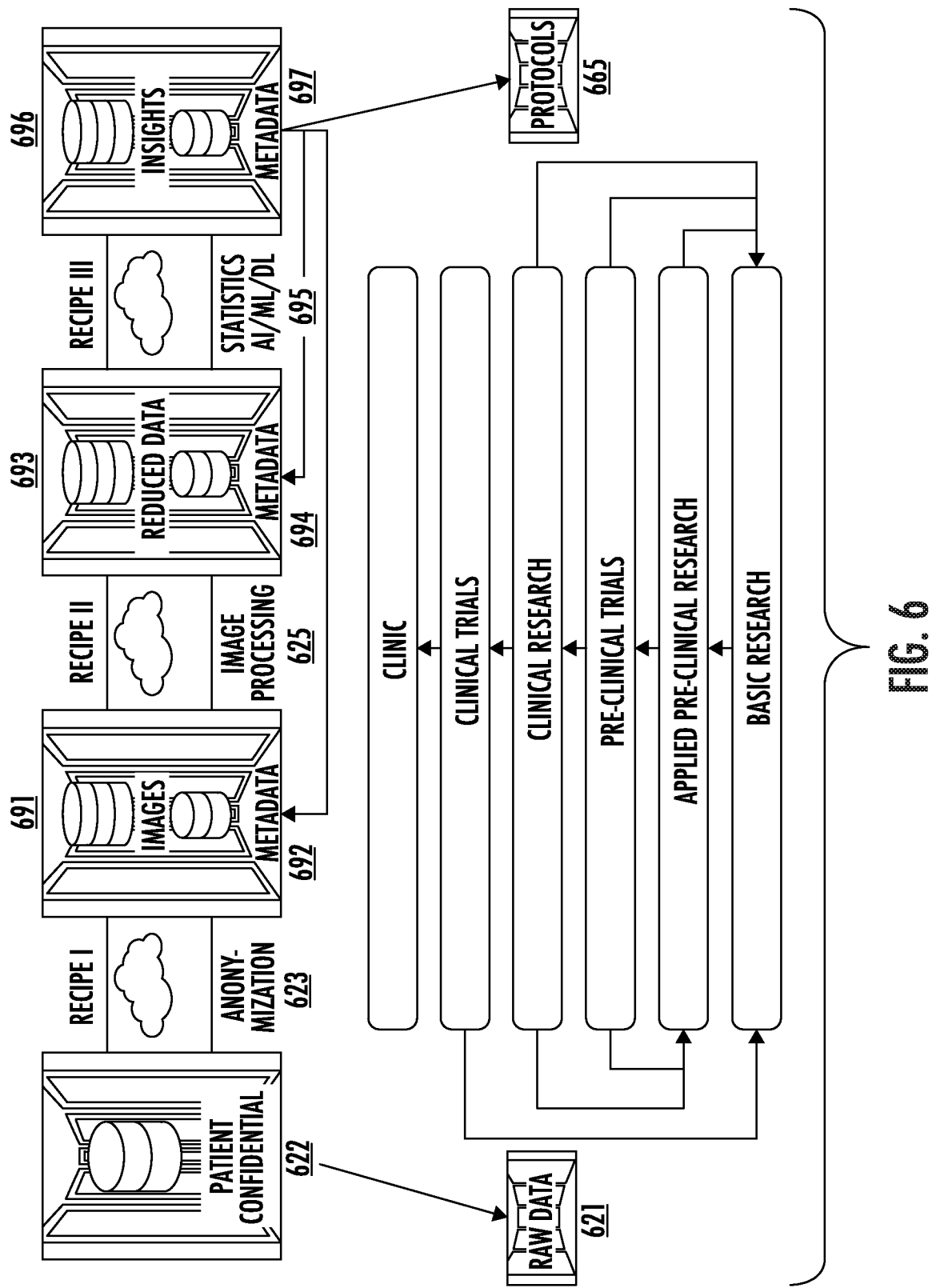
FIG. 6 is a diagram of the integrated system in accordance with some embodiments of the present inventive concept.

FIG. 6 is a block diagram illustrating an integrated system in accordance with some embodiments of the present inventive concept. As discussed above, embodiments of the present inventive concept use an image database including a large number of images and this image database may be a database of raw images 621. These raw images 621 may include patient confidential information 622 and metadata. Embodiments of the present inventive concept provide various engines to apply "recipes" to process the data so the data can be used for different applications. For example, an anonymization engine/module 623 may apply "recipe I" to remove all the "private" patient data. This anonymized data may split the raw data 621 into images 691 and metadata 692, the two data sets may be connected by a confidential key. At this point the images may be further processed by various engines, classification engine, mining engine, training engine, test engine, and validation engine. These various engines can process the data in a series of sequential steps and store derived results in a form traceable to the original data and to additional introduced data, and to the processing engines or rules, useful for the various purposes, and transparent with respect to order of events. Thus, embodiments of the present inventive concept provide a process for integrating "recipes" with data and intermediate to final outcomes, and automatically reprocessing all steps as additional data is added or as a recipe is modified.

For example, in some embodiments, the stored images may be annotated with comments from experts such as doctors and researchers. For example, an expert may annotate an image with a diagnosis, such as glaucoma. The images may also be shifted, rotated, de-noised and the like and such derived data may be stored with the perturbations, preferably as new copies such that the provenance of original images and data is fully preserved. As further illustrated in FIG. 6, "recipe II" may be an image processing 625 recipe and may provide a reduced image 693 and additional metadata 694. An example of the reduced image may be a segmentation map fully correlated to the original image, but without the pixel values of the original image. "Recipe III" may be a statistical recipe 695 applying deep learning and provide insights 696 and additional metadata 697. The preservation of metadata (692, 694, 697) provided at each step allows the algorithm in accordance with embodiments discussed herein to retrace its steps all the way back to the raw image date 621. All this data at any stage may be used to create and refine protocols 665. The data may be used in clinics, clinical trials, clinical research, pre-clinical trials, applied pre-clinical trials, basic research and the like.

Thus, data is accumulated, classified, anonymized, extracted and annotated and stored after the particular engine has performed its function. Once stored the images may be made available to the various users in a database(s). The images may be stored having various privacy levels, from public and open to proprietary, private, and closed. The private data may be stored behind an interface and require a key for entry.

As discussed above, the images may be prepared and studied. The database of images may be mined (queried) based on many factors including classification. The classified data may be segregated into sets according to various rules and the rules may change over time. Thus, the algorithms learn over time. For example, as data privacy laws change, so will the rules ("recipe") applied to the data when the data is being processed. The various data sets may be used to train/teach, verify test and validate. The validation set may preferably be segregated from the training and tests sets in order to confirm that the algorithm or recipe being validated has not been biased or contaminated by previous access to the validation data set. The algorithms or recipes are only validated when all tests have been met when tested on data that has not been previously used during training and testing. The data may be stored in a database accessible to the cloud so that the data may be used by others on the cloud.

In order to provide traceability to the large number of transactions, algorithms and recipes that may be applied to an image data set for the purposes of biomarker or diagnostic development, validation, regulatory clearance, and deployment, a clear, traceable record of all interactions with and operations on the data must be maintained. For example, a log may be generated that includes a sequence of operations combined with associated outputs. This may be differentiated from logs that provide a time stamp of interactions, but not the associated data records.

Furthermore, living-subject data generally requires security, respect of patient privacy rights, and agreements of limitations of use, disclosure, and financial transactions that involve the data directly or involve insights derived from the data. A record of all user interactions and use of the data must be maintained with consideration of the contracts that govern legitimate use of the data. These objectives point to two separate, if related, uses for ledgers to record histories of user access to data, and to record the processes of operations applied to data for the purposes of validating the discovery and development of new insights, diagnostics, and biomarkers and the like from the data. Blockchain ledgers are thus useful for recording data contracts and access, and for tracing operations on data during algorithm and recipe development and validation.

In particular, the blockchain is a growing list of records, called block, which are linked using cryptography. Each block contains a cryptographic hash of the previous block, a timestamp, and transaction data. In other words, the blockchain is a system of distributed ledgers used to store records of transactions. Think of it as a database, but instead of storing a single version of the database on one computer or server, everyone involved in the blockchain has their own copy of the same ledger. The blockchain is so named because it consists of a series of "blocks." As transactions are completed, new blocks are added to the chain. Thus, is someone wants to change something in the blockchain, all (or mostly all) the ledgers must agree before the change can be made. Thus, storage in the blockchain is secure and the security is difficult to breach. Blockchain structures in the context of the proposed workflow, image management, and image processing platform are thus particularly useful in distributed, multi-site environments that are the norm in clinical research and development.

Referring again to FIG. 6, embodiments of the present inventive concept may allow the image data to be accessible in various forms to various users, for example, clinic, clinical trials, clinical research, pre-clinical trial, applied pre-clinical research, basic research and the like. Providing the various engines to process the data before it is stored allows the data to be provided in a usable format for each user without violating privacy laws.

Some embodiments of the present inventive concept provide an image management system for the development and validation of diagnostic endpoints. In some embodiments, the system includes a static database containing static records for individual images. The records may include a reference code that is unique to the image and distinct from patient identifying information; a series of fields that define the equipment from which the image was acquired; a series of fields that define the site at which the image was acquired; a series of fields that define the demographics of the subject of the image; and a series of fields that define known subject condition attributes.

In further embodiments, a database containing dynamic records for individual images may be provided. The record may include a history of the access to the image, a history of algorithms applied to the image for the purpose of deriving a reduced set of data from the image; the existence and location of a reduced set of data derived from the image; a history of annotations applied to the image for the purpose of applying an expert comment to the image; and the existence and location of the expert comment applied to the image.

Still further embodiments provide a processing engine to validate the de-identification and protection of subject privacy. The privacy engine includes a set of rules applied against the static or dynamic database records that test for the presence of subject identifiable content and that applies a flag to the image, the static database, or the dynamic database that indicates the presence of lack of subject identifying content.

Some embodiments provide a processing engine to select from and apply one or more algorithms to modify an image according to a set of algorithmic objectives, to derive a reduced set of data unique to the image, or extract derived attributes from images, and to store the algorithmic steps, the modified image, the reduced data set, or the derived attributes for recall without modifying the original image.

Further embodiments of the present inventive concept provide an engine to provide selected images engines, original or images as modified by the Image Pre-processing Engine, to a subject matter expert and to collect annotations provided by the subject matter expert. The annotations become a record within the static or dynamic database.

Still further embodiments of the present inventive concept provide a processing engine to classify and index one or more images against a multiplicity of fields from one or more of the databases, including based on annotations developed through pre-processing in the expert annotation engine. The classification describes commonality of attributes against which future subjects are tested.

Some embodiments provide a randomization engine to select a multiplicity of images according a classification, select images according to a randomization algorithm, flag each of the multiplicity of randomized images uniquely into one of three or more sets. One set of images is used for training of an automated image processing algorithm, one set of images is used for testing the trained algorithm, and one set of images is used to validate the trained algorithm.

Various populations may be defined. For example, population 1 (optional) is a population of normal or controls; population 2 (required) is a training population of subjects in like classification and in unlike populations used to develop an algorithm for including future subjects into classification; population 3 (required) is test population of subjects in like classification and in unlike populations used to test algorithm during development for including future subjects into classification; and population 4 (required) is a validation population; blind population of subjects that are graded to be within or without the target classification, against which the final trained algorithm may be tested for accuracy (sensitivity and specificity) using known methods of analysis. In some embodiments, the embodiments of the present inventive concept automate the segregation of available data into these various populations using random assignment, with the support of user-defined proportions of data to be set aside into the various populations. The use of the data is then traced and recorded, for example, in the blockchain ledger of transactions and operations.

Still further embodiments provide an interactive pre-processing engine that operates on a training population set aggregated from the Deep Learning randomization engine, to perform one or a multiplicity of steps to establish features, or attributes from an original image, a modified image, or a derived data set from images that are indicative of a classification that is to be automated by the Deep Learning engine.

Some embodiments provide a batch processing engine that applies a recipe consisting of one more algorithms applied in parallel, sequentially, or in combination to at least one set of images that are a full set of images chosen from by the randomization engine or a subset of such a set.

Further embodiments provide a processing engine to create an automated image classification algorithm that operates on images using a series of pre-processing steps defined by the processing engines of the subject system, to classify images in a manner that matches the classification scheme defined in the system, and is validated or validatable by subject matter experts substantially equivalently to annotation of the training image set.

Still further embodiments provide a decision engine that provides a binary output stating that a classification test returns a positive or negative result with respect to the target classification.

Some embodiments provide a visualization engine that displays one or images, an indication of the classification of the image as drawn from the static or dynamic database, and a result of the algorithm or recipe.

Further embodiments of the present inventive concept provide a statistical test engine that performs one or more statistical tests of the result of a recipe or algorithm applied to a set or subset of images.

Still further embodiments provide a workflow recording engine that maintains and records a series of operations used from among the processes of de-identification, classification, randomization, batch processing, decision making, visualization, and statistical testing. In other words, some embodiments provide a workflow database that stores data, images, processes, algorithms, decisions and the like.

Some embodiments provide a workflow editing engine that presents a visual representation of the ordered set of the recorded workflow steps as a list or as a set of graphical elements that may be edited, truncated, added to, or reordered to create a different workflow. Editing may include different steps or may allow selection of different data, or application of different algorithms, or application of different statistical tests or the like. Thus, some embodiments allow graphical visualization of workflow and graphical re-ordering of sequence of events for reprocessing to be incorporated into the workflow database itself.

Further embodiments provide a workflow replication engine that reruns an original or edited workflow on a previous, modified, or new data set.

Still further embodiments provide a validation accumulation engine that runs a previous workflow on a new data set and combines the results into a new statistical test that includes in its population a previous data set and the new data set.

Figure 7:
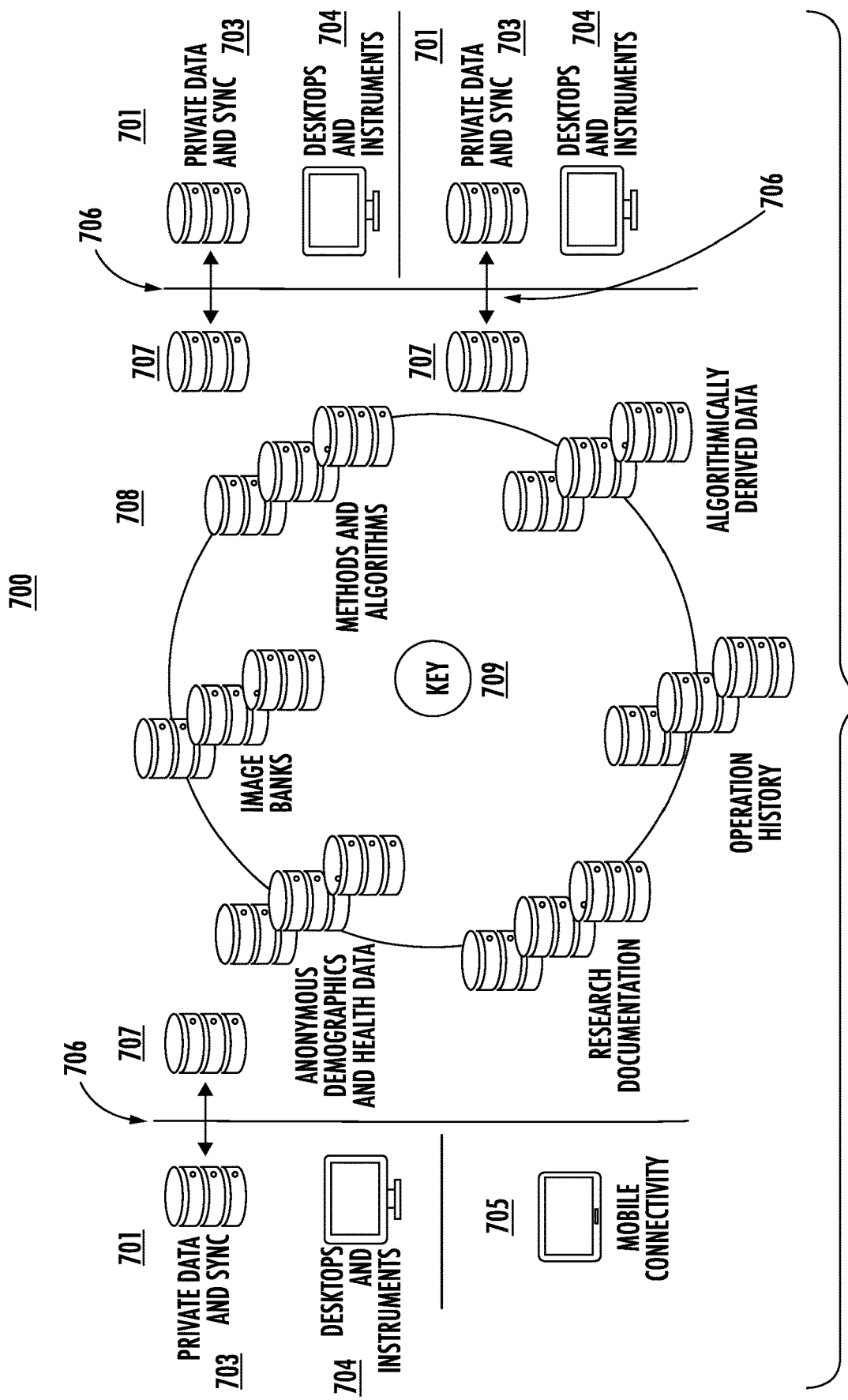
FIG. 7 is a block diagram of an integrated system in accordance with some embodiments of the present inventive concept.

Referring now to FIG. 7, an example embodiment of an integrated system for processing and using images acquired of subjects in a research or clinical environment in accordance with some embodiments of the present inventive concept will now be discussed. Although FIG. 7 illustrates a system including various modules/devices inside and outside the cloud, embodiments of the present inventive concept are not limited to this configuration. For example, there may be more or less than three private data sources without departing from the scope of the present inventive concept.

As illustrated in FIG. 7, the system 700 includes a plurality of private systems 701 including communications equipment 704 and private data storage 703; a mobile connectivity module 705, a plurality of pre-processing engines 706 between the private systems and a cloud storage module 707 and various modules (algorithms, derived data, historical data, research documentation, de-identified data and the like) and data storage (anonymous data and image banks) in the cloud 708. As discussed above, the system 700 illustrated in FIG. 7 is provided for example only and should not limited embodiments of the present inventive concept. It will be further understood that the information discussed with respect to the system 700 could be stored in a blockchain environment and used accordingly.

Referring to FIG. 7, the plurality of private systems 701 include private data stored in an image and data bank 703. This data and the associated images are generally raw data that includes information (metadata) that indicates the source of the data, when the data was collected and the like. In other words, the image and data bank may include, for example, raw images originating from one or more image-generating devices and/or storage devices, data associated with the raw images, and data associated with imaged subjects. The image-generating device may be any device known to those of skill in the art without departing from the scope of the present inventive concept. The private data 703 is associated with a workflow management module, for example, LATTICE, which is configured to configured to transport the raw images directly from the one or more image-generating devices and/or storage devices to the image and data bank and to manage and analyze the raw images, data associated with the raw images and the data associated with the imaged subjects in the image and data bank. In embodiments utilizing LATTICE, the functionality thereof is known and, therefore, the details of the LATTICE module will be discussed further herein.

As further illustrated in FIG. 7, a pre-processing engine 706 is positioned between the workflow management module in the private system and a cloud storage module 707. The pre-processing engine 706 is configured to receive the raw images, data associated with the raw images and the data associated with the imaged subjects from the workflow management module and process the raw images, data associated with the raw images and the data associated with the imaged subjects to provide the processed images and data before the processed images and data are pushed into the cloud storage module 707. The cloud storage module 707 is configured to store the processed images and data from the workflow management module.

In some embodiments of the present inventive concept, at a minimum, the pre-processing engine 706 anonymizes (de-identifies) the raw images, data associated with the raw images and the data associated with the imaged subjects to provide de-identified images and data to the cloud storage module 707 and create a key 709 that relates the raw images, data associated with the raw images and the data associated with the imaged subjects to the de-identified, processed images and data. The key 709 remains separate and unconnected from the de-identified, processed images and data in the cloud storage module 707. The key 709 allows the de-identified, processed images and data to maintain traceability to the imaged subjects and to all subsequent operations on the images and data.

In other words, in operation, the various private systems 701 (or sites) use a workflow management system (e.g. LATTICE) to push data into the cloud. However, embodiments of the present inventive concept provide a pre-processing engine 706 between the workflow management system in the private system 701 to de-identify data (anonymize) the data before it is provided to the cloud storage system 707. The data stored at private system/workflow management system is structured, for example, in folders and subfolders. This data may be stored in a relational or structured query language (SQL). The data pushed into the cloud may be stored using unstructured data methods (NOSQL, MongoDB, Cassandra, and the like) in the cloud storage module 707. Each specific imaging or data acquisition device may have a unique application protocol interface (API) that communicates between the device and the workflow management system, with the workflow management system mediating communication with the cloud. For example, LATTICE may have APIs for every unique device, such as a Zeiss Cirrus Optical Coherence Tomography imaging system as distinct from a Heidelberg Spectral is Optical Coherence Tomography imaging systems, as further distinct from and Optos Optomap Widefield Fundus imaging system, that include specific instructions for that device. In some embodiments, an indicator may be set in a data field that tells the system which API should be used. In some embodiments, the APIs may be stored at the pre-processing engine 706 so that the APIs can be timely updated. However, in certain embodiments the API may be provided as an application without departing from the scope of the present inventive concept.

The pre-processing engine 706 is not limited to just anonymizing (de-identifying the data). The pre-processing engine 706 is configured to receive the raw images and data from the workflow management module, determine a specific set of instructions (as discussed above) associated with the received raw images and data from the workflow management module; and process the received raw images and data based on the specific set of instructions associated with the received raw images and data from the workflow management module. The data may be validated, quantified, annotated, classified, anonymized and undergo other pre-processing steps in accordance with embodiments discussed herein before being distributed to the cloud storage module 707. As discussed above, the data stored in the cloud storage module 707 is de-identified and unstructured, i.e. no folders, subfolders and the like. In some embodiments, pre-processing may include more than de-identification, for example, data may be stored according to rules that would not be obvious to an outside observer.

As discussed above, when the data is de-identified, a key 709 is created, which remains outside the cloud. The key may be created in the pre-processing engine, but it is stored separately from the data itself. Some embodiments of the present inventive concept contain a pollution control function/module that includes a list of rules that removes all "non-essential" data. Whether the data is essential or non-essential can be determined on a case by case basis. The data that is removed may not be discarded or recycled, but kept, until a user indicates with the data should be stored, discarded or the like.

The pre-processing engine 706 allows complete control and providence over the data. The pre-processing engine can be viewed like a mailbox. A user provides the data and the pre-processing engine 706 anonymizes, restructures and the like and puts the data where it is supposed to go, for example, in the cloud or back in the structured database. It is advantageous to store the data in both structured and unstructured databases as some data lends itself to structured databases and other types of data lends itself to unstructured data. For example, images lend themselves to unstructured formats. If you put images in folders, you may not find the specific data/image you are looking for unless the specific search is performed.

As discussed above, the cloud may include various modules that can access the data stored in the cloud storage module 707 and used that data for various purposes. For example, one module in communication with the cloud storage module 707 may be configured to apply a set of rules to at least a portion of the images and data stored in the cloud storage module (methods and algorithms). This list of rules may be an algorithm implemented by a module in the system. This same module or a different module may be configured to apply a series of algorithms (a recipe) to at least a portion of the images and data stored in the cloud storage module. Another module may be configured to use at least a portion of the images and data stored in the cloud storage module and derive new images and data therefrom (derivation module or algorithmically derived data). For example, the derivation module may be configured to, for example, assess quality of the images and data; reduce noise in the images and data; segment the images and data; and/or measure the images and data. The quality of the data may be examined prior to distribution to storage.

As further illustrated in FIG. 7, other modules may include modules directed to research documentation, operation history and the like without departing from the scope of the present inventive concept. As illustrated by the circular arrangement of the modules in FIG. 7 (as well as FIGS. 4 and 5 discussed above). The images and data stored in the cloud storage module are constantly updated by various modules in the cloud. In other words, the data is reused and replicated and derived data modified over and over (with the original data preserving full original provenance). In some embodiments, the modules in the cloud utilize one or more of artificial intelligence (AI), statistical abstraction; image abstraction and image extraction to provide derived data. In some embodiments, one of the modules in the cloud may be provided by MOSAIC. The images and data stored in the cloud storage module 707 may include, for example, statistical data; processed images; reduced images; retrospective images; in vivo images; in vitro images; functional test results; and biospecimen test results.

The system's ability to maintain complete traceability (operation History), i.e. maintaining the providence of all the data is advantageous. In other words, any data can be recreated, backwards and forwards and, thus, the raw image can always be recreated. As discussed above, in some embodiments of the present inventive concept, one or more aspects of may be stored in the blockchain. Use of the blockchain will enable the traceability feature of all operations on the data as well as simplify regulatory audits. Furthermore, the blockchain may also enable keeping a record of anyone who has accessed the data or has access to the data. If an unauthorized person sees the data, takes the data or is given the data, the system records this information for a user's consumption.

As discussed above, some embodiments of the present inventive concept use MOSAIC to process data, for example, randomize, segment and the like. In some embodiments, MOSAIC may be used to create new algorithms and recipes and push them into the module for algorithms and recipes in the cloud. However, it will be understood that embodiments of the present inventive concept are not limited to this configuration.

In some embodiments, the image and data bank includes ophthalmic images and data, however, it will be understood that embodiments of the present inventive concept are not limited to this configuration. Any type of images and data may be used without departing from the scope of the present inventive concept.

As discussed above, some embodiments of the present inventive concept provide an integrated system for collecting, managing and mining images and data that may be regularly updated and refined and using the images and data together with any of the subsequently derived data for the training, testing, and validation of algorithms. These algorithms may be used, for example, for the development of markers of disease and disease progress, markers of physiological response to internal and external factors including therapeutic interventions, correlation of phenotypes with genotypes, and development of diagnostic and prognostic measurements and methodologies.

Figure 8:
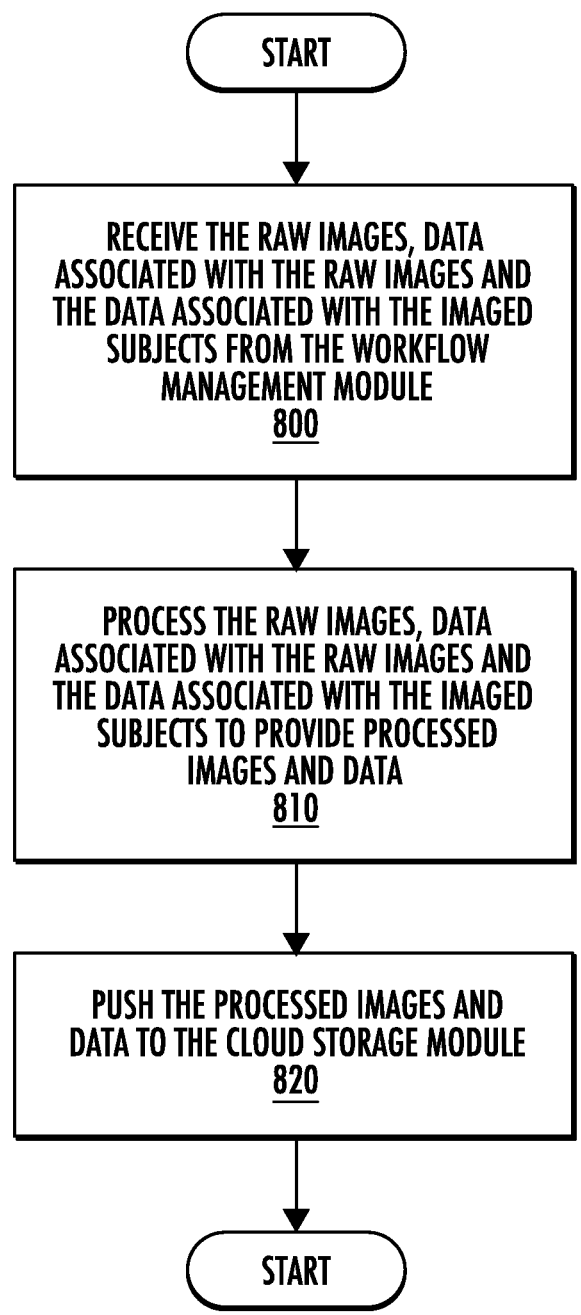
FIG. 8 is a flowchart illustrating operations in accordance with some embodiments of the present inventive concept.

Referring now to the flowchart of FIG. 8, high level operation for a processing data at a pre-processing engine will be discussed. The operations illustrated in the flowchart of FIG. 8 are directed to a method for processing and using images in a system. The system including an image and data bank including a plurality of raw images and associated data; a workflow management module in communication with the image and data bank and configured to manage and analyze the raw images and data in the image and data bank and a cloud storage module in a cloud configured to store the images and data from the workflow management module. Operations begin at block 800 by receiving the images and data from the workflow management module. As discussed above, structured data is stored at a private site in the system. The workflow management module (LATTICE) processes the data and forwards the structure data to a pre-processing engine. The pre-processing engine processes the images and data before the images and data are pushed into the cloud storage module (blocks 810 and 820). The cloud storage module is configured to receive the processed images and data. At a minimum, processing the data includes anonymizing the images and data to provide de-identified data to the cloud storage module and creating a key that remains separate from the processed images and data. The key allows the images and data to maintain traceability both forward and backward.

The pre-processing engine may receive the raw images and data from the workflow management module; determine a specific set of instructions associated with the received raw images and data from the workflow management module; and process the received raw images and data based on the specific set of instructions associated with the received raw images and data from the workflow management module. The specific set of instructions associated with the received raw images and data may be determined by an indicator set in a data field. The indicator may identify a specific set of instructions for the received raw images and data from a particular device.

In some embodiments, the pre-processing engine may remove non-essential or private data from the raw images and data; store the removed non-essential or private data; and, before recycling the non-essential or private data, request permission from a user associated with the raw images and data. The rules for this anonymization may be prevailing Health Insurance Portability and Accountability Act (HIPAA) rules (USA), GDPR rules (EU), and the like, and the set of rules applied may be themselves stored as traceable data elements, such that data may be re-anonymized as rules change over time.

After the data is processed and pushed to the cloud, the data may be used by various modules, the modules may apply a set of rules to at least a portion of the images and data stored in the cloud storage module; apply a series of algorithms to at least a portion of the images and data stored in the cloud storage module; and/or using at least a portion of the images and data stored in the cloud storage module to derive new images and data therefrom.

As further discussed above, the data is constantly being updated, thus, the steps of the method are repeated to constantly provided updated images and data.

Example embodiments of the systems discussed above will now be discussed. In these embodiments, the system integrates the desired data structures and workflows under a unified platform with a common point of access. These embodiments of the present inventive concept allow integration of source data, including protocols and approvals, subject consents, subject metadata and historical medical history, exam management, exam test results and images, protect health information management, data cleaning and pre-processing, automated and directed data collection management for diagnostic and research applications, multimodal data visualization, visualization and quantification through algorithm libraries, together with workflows for sharing and collaboration based on a library of licenses, development and validation of image processing, artificial intelligence, and deep learning algorithms, workflow definition with sharing and reuse, a multidimensional set of transaction records for monitoring data access and data operations, automated organization of history files to support analysis projects to meet publication or regulatory objectives, all within one interoperable platform that serves the widest body of users according to the variety of roles associated with image based translational research, clinical management, and visual autonomous decision support.

The architecture of the system discussed herein provides an advantage over a generic Clinical Trial Management Software (CTMS) solution, such the system discussed in *Utilization of a Clinical Trial Management System for the Whole Clinical Trial Process as an Integrated Database: System Development* to Park et al., the disclosure of which is hereby incorporated herein by reference as if set forth in its entirety. Park discusses a very detailed analysis of the benefits and challenges associated with the development and utilization of a CTMS solution. As noted in Park, efficiency in clinical trial management at the site level, where data is collected, is challenging dues to the high administrative burden, dysfunctional communications, lack of real-time data access, limited resources, risk of protocol and regulatory noncompliance, and the difficulty of accurate reporting.

Figure 9:
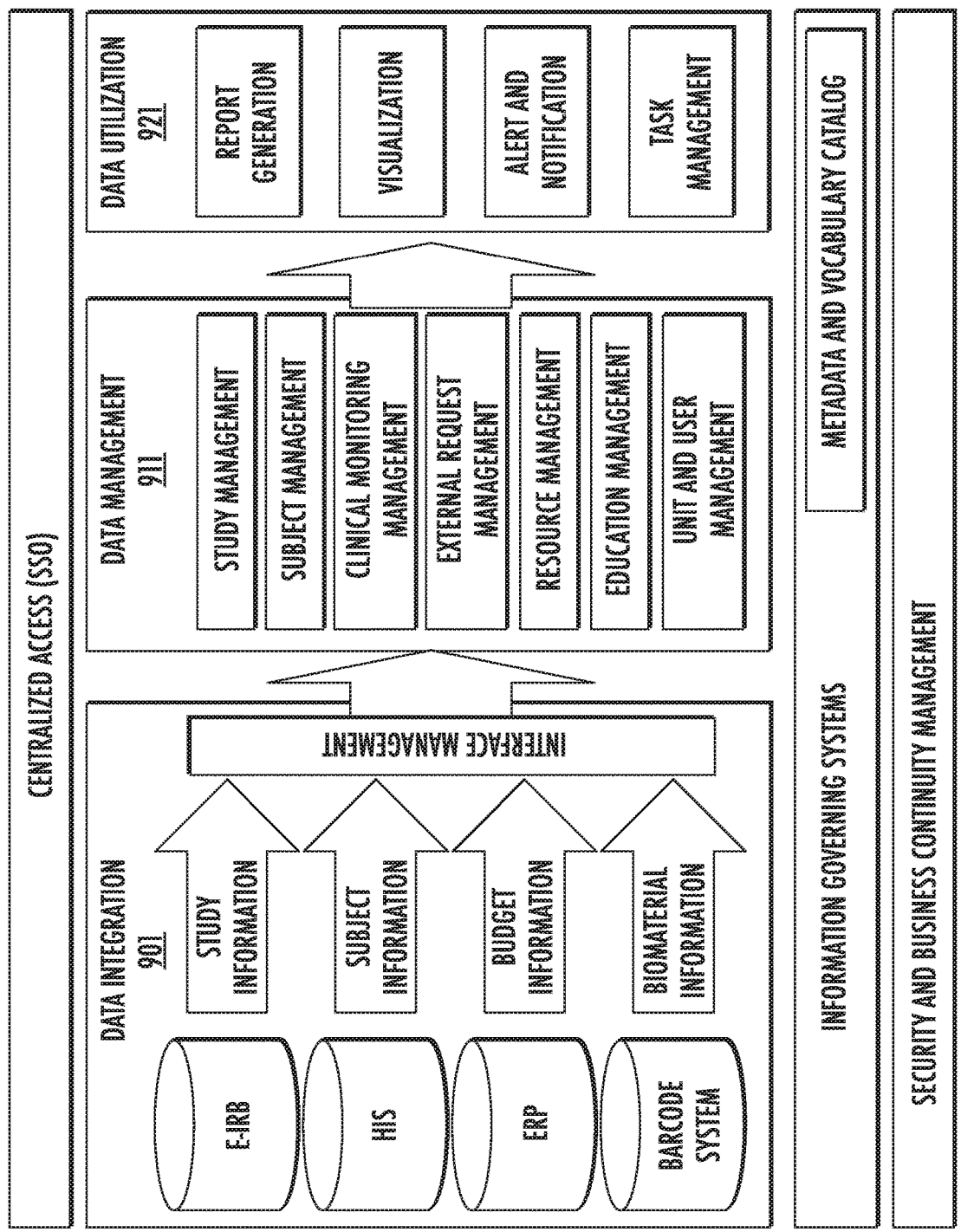
FIG. 9 is a block diagram of a system architecture designed around a three-layered workflow: data integration, data management, and data utilization.

Referring now to FIG. 9, the system discussed in Park will be discussed. As illustrated in FIG. 9, the system architecture deployed in Park is designed around a 3-layered workflow: data integration 901, data management 911, and data utilization 921. Data integration 901 includes the sources of data inputs, including electronic Institutional Review Board (e-IRB), Health Information Systems (HIS), Enterprise Resource Planning systems (ERP), and a barcode system. Data integration 901 communicates with data management 911 through an interface therebetween. Data management 911 includes study management, subject management, clinical monitoring, external request management, resource management, and user management. Data utilization 921 includes report generation, visualization, notifications, and task management.

As noted in Park, such a CTMS simplifies the process of managing and tracking clinical trial progression within a site, for example, an academic medical center, improving communications between the variety of stakeholders involved in any trial. LATTICE, the pre-cursor to embodiments discussed herein, performs the role of such a CTMS. As alluded to in Park, CTMS solutions are intended to hand off data for analysis to either the managing Contract Research Organization (CRO) or sponsor, and as such CTMS solutions are not generally effective tools for analyzing research data (other than the business analytics), and are certainly not suited to the development of new trial outcome measures and endpoints. Further, these systems are generally not suited to retrospective deployment of the data accumulated during a specific project or trial.

In stark contrast, system in accordance with embodiments of the present inventive concept reflect a significant extension to CTMS architectures that addresses many of these aforementioned shortcomings of conventional systems as will be discussed with respect to FIG. 10. Example architecture in accordance with some embodiments of the present inventive concept will be discussed with respect to FIG. 10, focusing on the additional capabilities provided by embodiments of the present inventive concept over conventional systems such as CTMS. These additional capabilities may be captured in the blocks outlined with bolded lines. However, it will be understood that operations in the other boxes may also be improved without departing from the scope of the present inventive concept.

Figure 10:
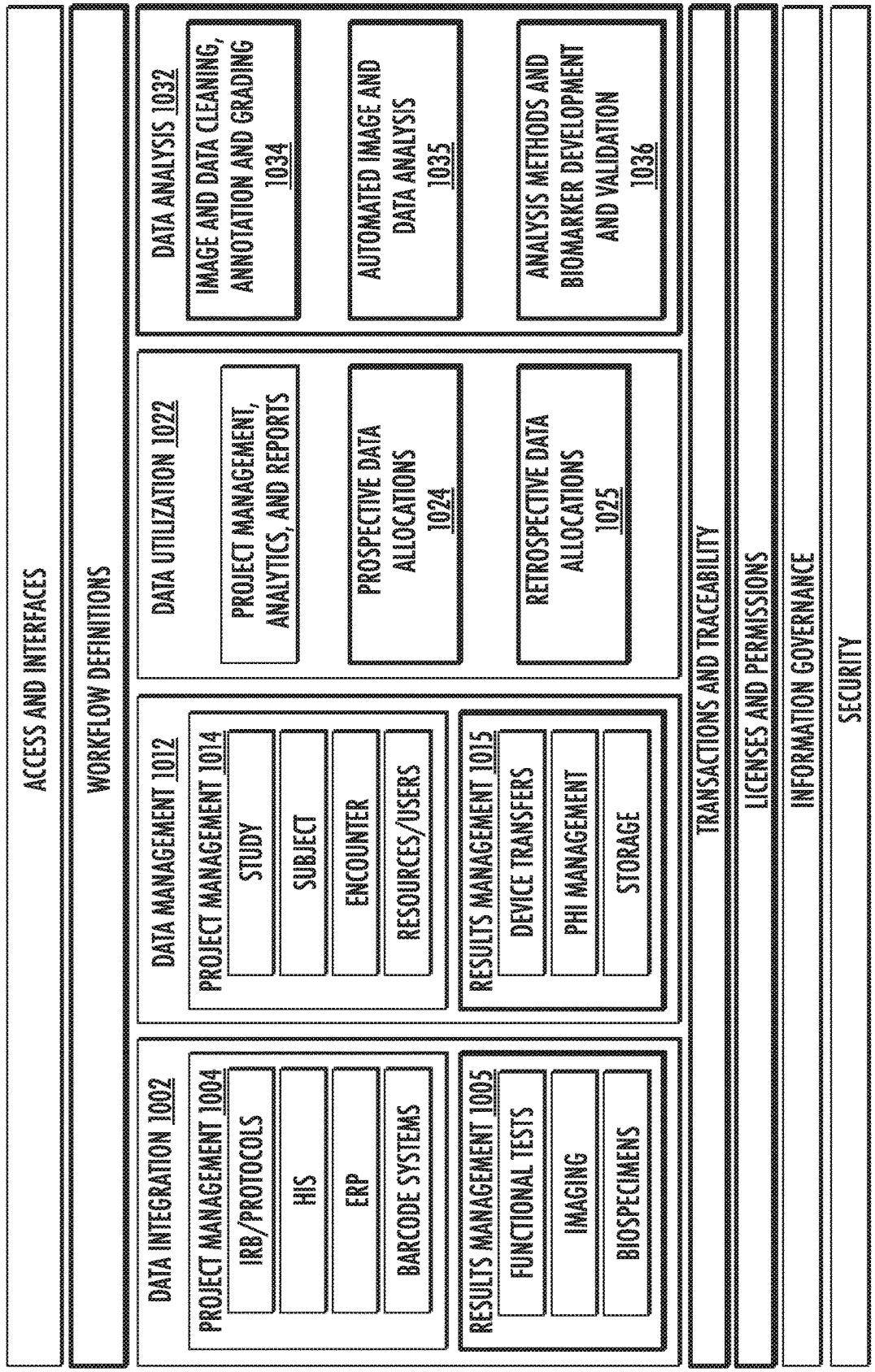
FIG. 10 is a block diagram illustrating system architecture in accordance with some embodiments of the present inventive concept.

As illustrated in FIG. 10, the workflow in accordance with embodiments of the present inventive concept include data integration 1002, data management 1012 and data utilization 1022 similar to the conventional system of FIG. 9, but system discussed herein further include data analysis 1032. Furthermore, each of the similarly labeled elements data integration 1002, data management 1012 and data utilization 1022 include additional bolded portions that provide various functionalities in accordance with embodiments discussed herein. For example, beginning with data integration 1002, in addition to project management 1004 (IRB/protocols, HIS, ERP, and Barcode systems) embodiments of the present inventive concept include results management 1005 including functional tests, imaging and biospecimens. In a conventional CTMS system, results are tabulated and recorded on forms that may be uploaded to the CTMS data tables. Embodiments of the present inventive concept are configured to capture raw data from devices and manage the raw data (source data) along with the tabulated data. Broadly, the source of raw data is depicted in FIG. 10 as functional tests, Imaging, and Biospecimens. Because of the extremely wide variety of tests in use, a general system that captures raw data generically has not been possible.

As further illustrated in FIG. 10, in addition to project management 1014 (study, subject, encounter and resources/users), that data management 1012 workflow further includes a results management section 1015 including device transfers, PHI management and storage. Similarly, in addition to project management, analytics and reports, the data utilization workflow includes prospective data allocations 1024 and retrospective data allocations 1025. The new workflow of data analysis 1032 includes three modules 1034, 1035 and 1036. The first module 1034 includes image and data cleaning, annotation and grading. The second module includes automated image and data analysis. The third module 1036 includes analysis methods and biomarker development and validation.

As further illustrated in FIG. 10, the various modules of data integration 1002, data management 1012, data utilization 1022 and data analysis 1032 interface with other modules including access and interfaces, workflow definitions, transactions and traceability, licenses and permissions, information governance and security to provide various aspects of the present inventive concept.

Figure 11:
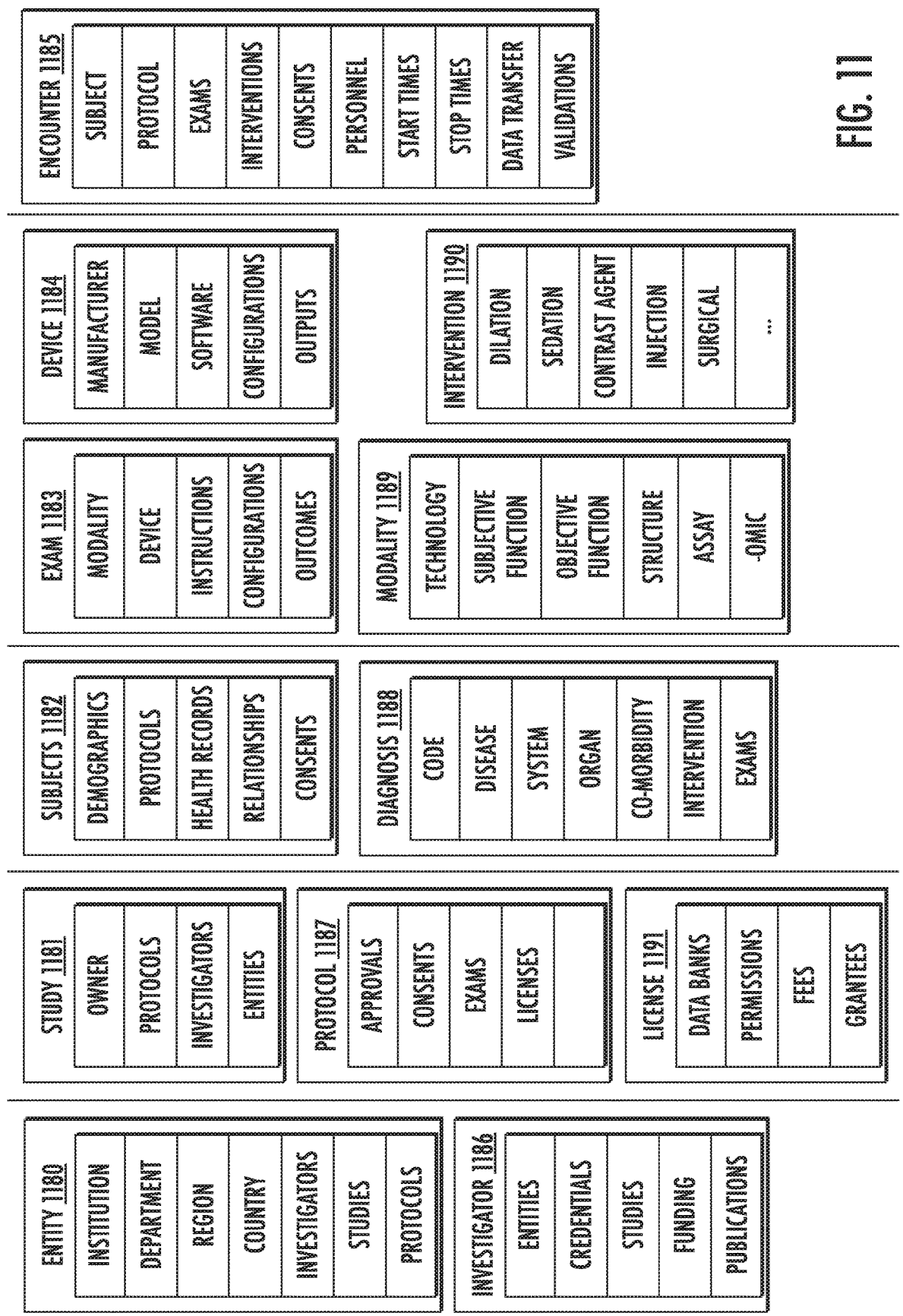
FIG. 11 is a block diagram illustrating a representation of a logical library that is enabled by embodiments of the present inventive concept.
Figure 12:
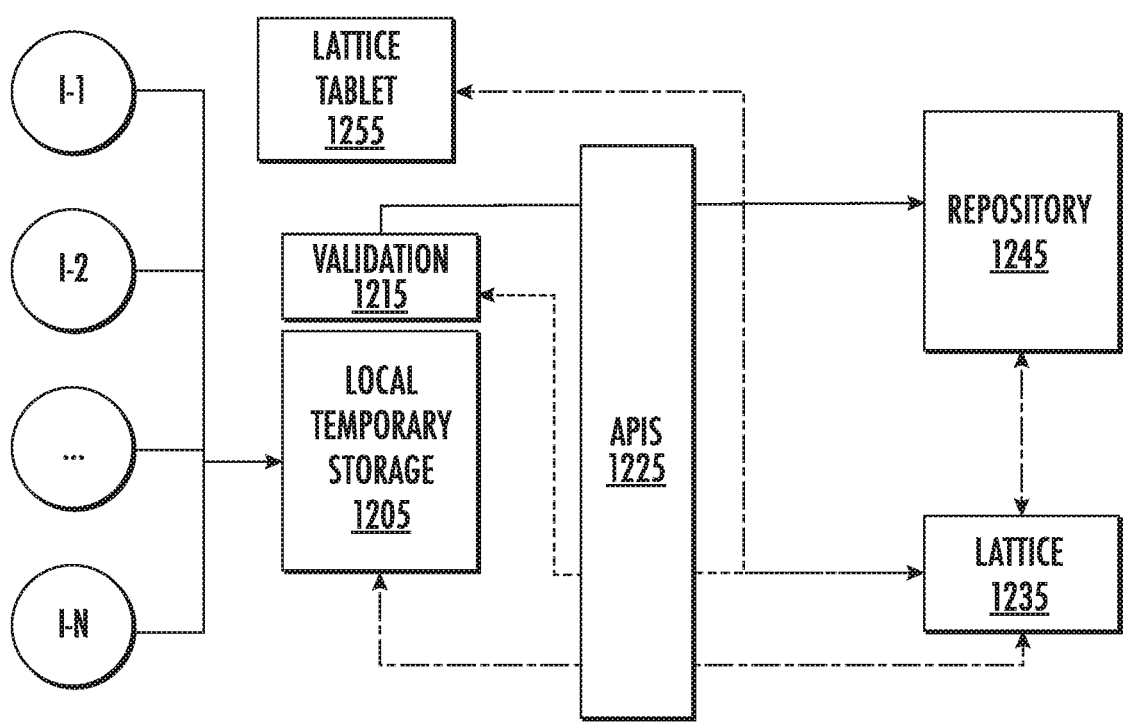
FIG. 12 is block diagram illustrating example communication interfaces that control movement of image data from local temporary storage a repository using application protocol interfaces (APIs) in accordance with some embodiments of the present inventive concept.

In some embodiments of the present inventive concept, a library may be used to inform embodiments, a representation of a logical library that is enabled by embodiments of the present inventive concept is illustrated in FIG. 11. For example, a library of Exams 1183 may be attached to a specific trial Protocol 1187. Exams 1183 can specify a Modality and are specific to a Device (FIG. 11). As illustrated, an Exam 1183 may further include Instructions, Configurations, and Outcomes (FIG. 11) in some embodiments. As used herein, a "modality" 1189 may refer to a Technology, a Subjective Functional Assessment, and Objective Functional Assessment, a Structure, and Assay, or an -omic. A "Device" 1184 may refer to a specific instrument for performing the Exam, and may include information as to Manufacturer, Model number, Software version, specific settings, Configurations, the type of Output and the like. The Exam 1183 may also be accompanied by an Intervention 1190. Embodiments of the inventive concept includes the hierarchical information structure to allow protocol-specific Exams 1183 to be managed in a logical library, for example, by Modality 1189, Device 1184, Intervention 1190 and the like, as for example, shown in FIG. 11. This library may be built to support specific domains, such as ophthalmology or optometry, but within an extensible and scalable architecture. FIG. 11 includes library architectures directed to entity 1180; study 1181; subjects 1182; exam 1183; device 1184; encounter 1185; investigator 1186; protocol 1187; prognosis 1188; modality 1189; intervention 1190 and license 1191. Each of the categories has one or more subcategories associated therewith. FIG. 12 provides an example library architecture and, therefore, embodiments of the present inventive concept are not limited thereto. Other categories and subcategories may be provided without departing from the scope of the present inventive concept.

Examples will now be discussed. In one example, an Exam 1183 may be an optical coherence tomography scan (OCT) of a retina. In this example, the modality is OCT. OCT provides an image of a structure of the retina. An OCT device may be a Zeiss (Manufacturer) Cirrus (Model) with a current software revision, configured to obtain a raster volume, with a portable document format (PDF) report output and a table of specified numerical results. The OCT exam may be preceded by an intervention to dilate an eye.

In some embodiments of the present inventive concept, a specific OCT Exam that reflects the requirement may be attached to a trial Protocol using a drag-and-drop graphical user interface element, and the results may be captured as will be discussed below. The Protocol may have specific requirements that are not present in the library of Exams. In such embodiments, the hierarchy of the Exam information is such that the Protocol coordinator may design an Exam from an OCT (Modality) template, or a Zeiss OCT template (Modality plus Manufacturer) or a Zeiss Cirrus OCT (Modality plus Manufacturer plus Model) and build out remaining details as necessary. The resultant specific Exam may become part of the Exam library, and the Library may be shared. Thus, the architecture is continually changing and being updated based on the various aspects of real time tests and the like.

An important part of the Exam specification is the definition of the "outputs." Outputs may include specific numerical results that are entered into a form, or saved to a file on the device 1184 or saved onto external storage. Outputs may also include raw data as generated and stored by the Device 1184, pre-processed raw data, or fully processed data. For example, with respect to OCT and, in particular, Spectral Domain OCT, raw data may include the wavelength-dependent as acquired at the detector of a spectrometer. Pre-processed raw data may include the spectral information after linearization or normalization. Fully processed raw data may include the structural image derived from the spectral data after various processes including Fourier transformation are applied. The availability and utility of raw data depends on the Modality 1189, the Device 1184 and the Device Manufacturer, and the specifications in the Protocol, as well as on the information content that may be useful for research. It may be almost impossible to define a general template for raw data that would be acceptable to all stakeholders, and therefore a system for managing raw data that is flexible and traceable is highly valuable. The most common form of output is a Device-specific report, frequently stored in an image file, such as a PDF or portable network graphics (PNG), or perhaps stored in more accessible digital imaging and communications in medicine (DICOM) file. Thus, embodiments of the present inventive concept provide an integrated platform that is flexible and agnostic to file formats.

As indicated in, for example, Park, electronic interfaces may be available that allow a CTMS to integrate with electronic IRBs, Health Information Systems, or ERP systems, and the like. A universal integration system does not generally exist for results management. This is not to say that there are not systems for managing diagnostic tests, imaging, and biospecimens. However, these systems tend to be part of very specific workflow and tend not to integrate with CTMS. To the extent these systems are capable of interfacing, they generally are not equipped to manage the exchange of raw data, and therefore leave a wide gap in functionality. For example, Picture Archiving and Communications Systems (PACs) and Laboratory Information Systems (LIMS) manage the visual display of medical imager and the recordation of biospecimen test results, respectively.

In order to generalize the access to results data that may not be connected by, or through PACS, LIMS or such similar systems, embodiments of the present inventive concept couple the Exam 1183 specification record with a Data Management workflow engine that solves important gaps in data collection functionality. A mobile device with a software application may be used during data acquisition encounters, an encounter generally refers to a sequence of one or more Exams with Subject according to a Protocol. The mobile device, for example, a tablet, a mobile phone, a mobile watch, and like, includes tracking of the subject through the various Exams in a counter. As designed in Lattice, the mobile device allows tracking of start and stop times of a specific Exam, and the recordation, as with a form, of specific quantitative data and notes. As originally designed, Lattice does not provide a provision for transferring data, raw or otherwise, from a Device. Some embodiments of the present inventive concept include a communication vehicle to facilitate and/or record the transfer of the Device data to a storage location. This communication vehicle may include, for example, a wired or wireless communication with the Device that initiates a transfer sequence from the Device to storage location. The communication vehicle records additional information, including initiation and conclusion of transfer, and tagging the data and the database record uniquely to track and verify that the data that ends up in the target location.

An important and useful feature of this communication vehicle/method is that the coordinator responsible for the Exam does not need to know the details of where the data will be stored or have to maintain a written log of actions. This information related to the Exam is maintained within the record of the Protocol, Encounter, and Exam. The activity record may be semi-automated with user-initiated start and stop commands, but the desired behavior is automated. This aspect of the present inventive concept further lends itself to an automated record generation to validate completion of the Exam and transfer of the desired data. Such a record may be fully automated or initiated upon request.

In many cases, the coordinator of the Exam will not be able to trigger the Device to transfer data to the desired storage location. This may be because of lack of a cooperative utility within the Device, or because of a lack of network connectivity to the storage location. In some embodiments of the present inventive concept time and geotracking of actions coordinated with the exam follow the results record, as the person performing the exam physically transfers the data from the Device to a Local Temporary Storage (LTS) facility. Drawing analogy to a postal delivery system, the LTS is mailbox where the file is delivered, and the LTS in communication with the inventive Data and Workflow Management System (DWMS) draws on Protocol instructions and the action record to determine the destination for the data. It will be understood that in contrast to a postal delivery system, the person performing the Exam does not need to "address" the data. The address may be embedded within the Protocol—Encounter—Exam instructions for the trial.

Prior to delivering the data to its target destination, the LTS may apply a series of processing steps that further simplify the management of the trial and the data. First, the LTS, using instructions embedded within the specification of the Protocol and the Exam, removes protected health information (PHI) from the data. PHI may be present in a file name, within the header information of a digital file, or embedded as an image within an image, for example. The PHI removal instructions may be developed for the specific Outputs of specific Exams and stored in an appropriately accessible library. The appropriate PHI removal engine may be accessed from the network downstream from the data source and applied to the data upon receipt at the LTS.

Referring now to FIG. 12, a model of a system in accordance with embodiments of the present inventive concept will be discussed. In particular, FIG. 12 illustrates communication interfaces to control to movement of image data from local temporary storage to the REPOSITORY though LATTICE APIs in accordance with some embodiments of the present inventive concept. It will be understood that although the system is illustrated with LATTICE elements, embodiments of the present inventive concept are not limited to this configuration.

As illustrated, the system includes one or more devices I-1 to I-n, n being any integer, integrated with the system. As illustrated, the devices I-1 to I-n are coupled to local temporary storage 1205. The data from the device I-1 to I-n may be provided to a validation box 1215, which is configured to remove PHI and other instructions applied to data prior to distribution. The APIs 1225 are the various programming interfaces that allow flexible and functional integration of instructions and methods to the Data and Workflow Management System (DWMS) system. In these embodiments, Lattice provides the Data Management System and the Repository stores the data as the Data Storage System. The system of FIG. 12 illustrates the mobile device 1255 as a Lattice Tablet. However, it will be understood that any mobile communications device may be used to encounter management can be used without departing from the scope of the present inventive concept.

As patient privacy demands continue to evolve, the state of PHI removal, i.e. the algorithmic definition of the PHI engine, may be stored in a relational record to the data. As a regulation changes, or as the data is to be used in a location with different regulation, the PHI log may be read to assess the compliance to a new standard, and a new PHI removal engine may be applied.

Biometric information contained within is a potential concern. Fingerprints are currently recognized as identifiable PHI. Facial recognition is a definite concern. Further, there is the potential other image data or -omic data (genome) that are not deemed to be identifying today that may be considered protected information in the future. Therefore, the PHI removal engine may include a decimation engine or the like to dissemble the data into fractional elements that are stored separately. Such fractional elements may be used to protect patients, facilitate data transfers, or facilitate process automations. In some embodiments of the present inventive concept, the biometric decimation engine may be defined independently for specific Exams and maintained within the Exam library and applied automatically according the rules of the Protocol.

It will be understood that the Repository 1245 may store result data as well as the libraries for Exams, PHI removal engines, workflow instructions, trial document records, and any results of analysis, actions, and the like that form the history of interactions with data. Lattice provides the connectivity between Protocols, Exams, and various methods for governance and management. In practice, Lattice and the Repository may be maintained by a single relational database. However, in some embodiments of the present inventive concept, Lattice is relational or hybrid database, and the Repository is a collection of databases, and these databases are generally non-relational databases with key-value pairs that allow extensibility and scalability, and the maintenance of interoperability with Lattice. The Repository items may be segregated into types and stored independently at separate physical locations, in a multi-cloud architecture. Such a system provides flexibility for cost management while maximizing security.

Additional operations may be deployed in the validation engine 1215 of the LTS. A first operation may be to validate the data against expectations for the Exam. In the case of a faulty validation, the Lattice may signal the Examiner to address the problem. This set of expectations may be purely structural: is the file of the expected type and the size of the expected size? Or, there may be a more technical requirement on data quality, for example, image quality. The Validation engine 1215 for the specific Exam may include an algorithm for assessing image quality or may include an even more sophisticated recipe for determining the likelihood that the results meet the requirements of the trial. This data validation activity is a significant cause of delays and cost overruns in clinical trials, as the validation occurs at the CRO, and there may be significant delays between the Exam and the Validation. The present inventive concept dramatically improves the efficiency of this feedback process, reduces errors and compliance validations, and reduces the cost and difficulty of scheduling patients for re-exam.

Referring again to FIG. 11, the Data Utilization layer 1022 of the Data and Workflow Management System (DWMS) architecture provides a wholly new type of functionality within the context of clinical trial management specifically, and the general context of image management for image based autonomous decision support more generally. Whereas a more traditional CTMS or image management system may be thought of a state machine, for example, a scalar, or generalized accounting system for a clinical trial, systems in accordance with embodiments of the present inventive concept provide a workflow engine that supports defining, initiating, executing, and validating an extensible set of workflows driven from the state machine, and driving a complex set of activities that create a new state.

The conventional CTMS of Park appropriately reflects the intricacy and complexity of the Clinical Trial Management process. CTMS systems stop where algorithmic analysis begins. CTMS systems can certainly generate reports from their respective databases, but they cannot and do not extend to the sort of analysis that include expert annotations or labeling, expert grading, application of image processing algorithms, or the development of new algorithms, recipes, outcome measures, or biomarkers. Yet this analysis activity is the reason for the investment in the study. This handoff from CTMS to analysis is itself costly, prone to error, non-scalable, and incredibly inefficient.

In some embodiments of the inventive concept, allocation of data to experts according to the specifications of the Protocol may be automated. For example, a Protocol may specify one or more classes of data to be annotated, labeled or graded by one or more human experts. A Recipe is pre-defined that queries and filters the data according the to a Protocol, assembles all of the relevant data, which may be of single or mixed modality, into a trackable Collection, and allocates the data for review to the panel of experts. As the experts interact with the data presented, the system tracks the transactions and records the expert annotations, labels and grades as separate Projects for subsequent quality review and analysis. The system may randomize the data so that the order of interaction is not biased, and the system may include test data and repeated data to add to the quality control. All of this may be automated within Workflow layer of the Data and Workflow Management System (DWMS) System, and transactions and results are logged within the Transactions and Traceability layer of the Data and Workflow Management System (DWMS) of FIG. 11.

In some embodiments of the inventive concept, allocation of data to automated analysis tools (algorithms and recipes) is automated according to the specifications of the Protocol. Similarly, a Protocol may specify one or more approved computational algorithms to be applied to classes of data. A Recipe is pre-defined that queries and filters the data according to the Protocol, assembles all of the relevant data, which may be of single or mixed modality, into a trackable Collection, and allocates the data for algorithmic computation. The system tracks the transactions and records the results. The system may include test data and repeated data to add to the quality control. All of this is automated within Workflow layer of the Data and Workflow Management System (DWMS) and transactions and results are logged within the Transactions and Traceability layer of the Data and Workflow Management System (DWMS) of FIG. 11.

Figure 13:
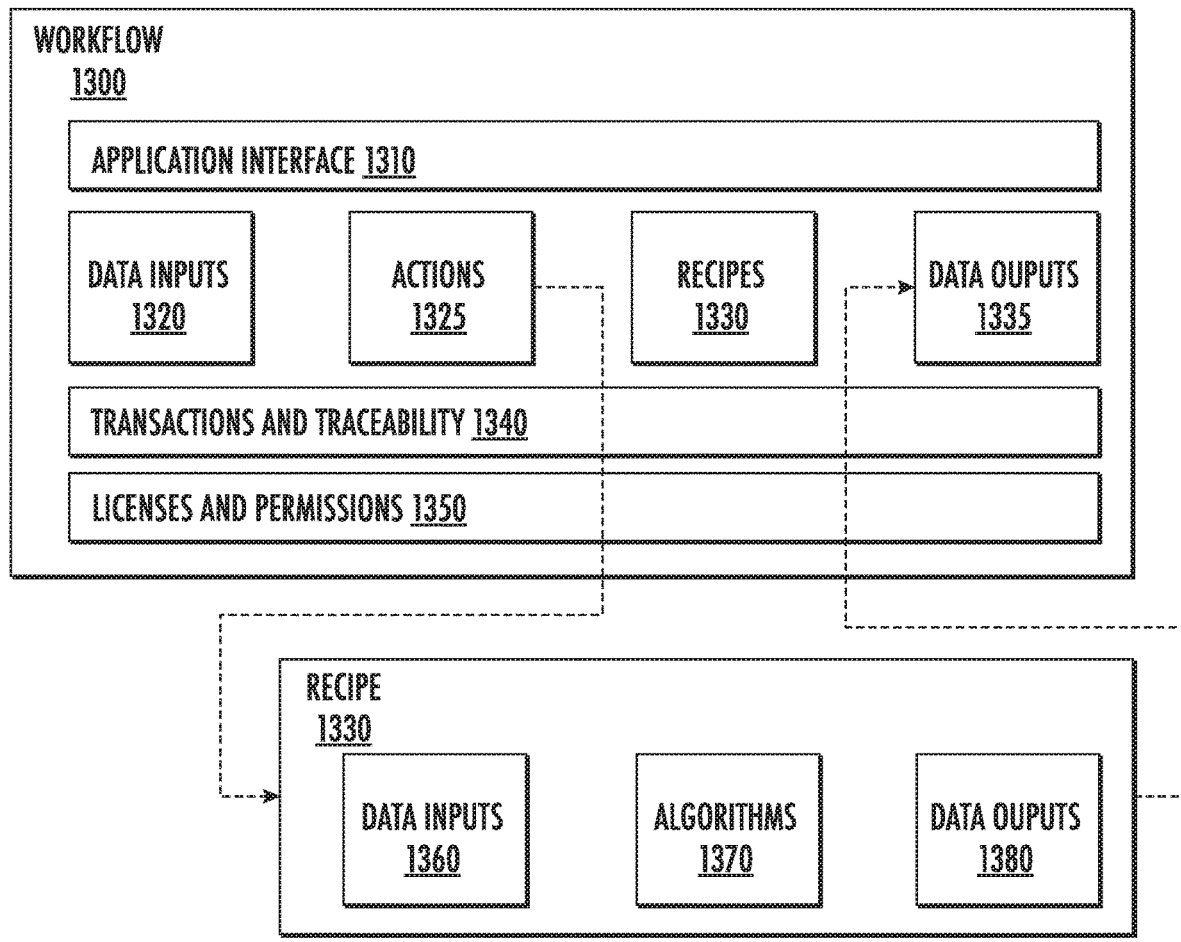
FIG. 13 is a block diagram illustrating a workflow that is a sequenced combination of data inputs, user Actions, the application of automated recipes, and data Outputs in accordance with some embodiments of the present inventive concept.

In some embodiments of the present inventive concept, a Workflow is a sequenced combination of Data Inputs, User Actions, the application of automated Recipes, and Data Outputs, as shown in, for example, in FIG. 13. Workflows are defined entries in the Data and Workflow Management System (DWMS), and are definable, copiable, editable, and shareable. As illustrated, the execution of a Workflow 1300 is enabled through the Application Interface 1310, tracked through the Transactions and Traceability layer 1340, and authenticated in the Licenses and Permissions layer 1350 of the Data and Workflow Management System (DWMS).

In some embodiments of the present inventive concept, a Recipe 1330 is a sequenced combination of Data Inputs 1320, automated Algorithms 1325, and Data Outputs 1335, and shown in FIG. 13. Recipes 1330 are defined entries in the DWMS, and are definable, copiable, editable, and shareable. The execution of a Recipe 1330 is enabled called by the Workflow 1300, tracked through the Transactions and Traceability layer 1340, and authenticated in the Licenses and Permissions layer 1350 of the DWMS.

In some embodiments of the present inventive concept, a Recipe 1330 is a sequenced combination of Data Inputs 1320, automated Algorithms 1325, and Data Outputs 1335, as shown in FIG. 13. Recipes 1330 are defined entries in the DWMS, and are definable, copiable, editable, and shareable. The execution of a Recipe 1330 is invoked by the Workflow 1330, tracked through the Transactions and Traceability layer 1340, and authenticated in the Licenses and Permissions layer 1350 of the DWMS. Definitionally, a Recipe 1330 is fully automated and invoked by a Workflow 1300 that may include user actions.

In some embodiments of the present inventive concept, an Algorithm 1370 implemented by a module is a set of computational operations that relies on a set of data inputs 1360 and yields a set of data outputs 1380. Algorithms 1370 are defined entries in the DWMS, and are definable, copiable, editable, and shareable. The execution of an Algorithm 1370 is invoked by a Recipe 1330, tracked through the Transactions and Traceability layer 1340, and authenticated in the Licenses and Permissions layer 1350 of the DWMS. Definitionally, an Algorithm 1370 is fully automated and invoked by a Recipe 1330.

In some embodiments of the present inventive concept, Algorithms 1370 may be tailored to unique applications by binding into unique Recipes 1330. Algorithms and Recipes may be developmental or validated and may be tagged as such in the DWMS and managed as such through the License and Permissions layer 1350 of the DWMS.

Figure 14:
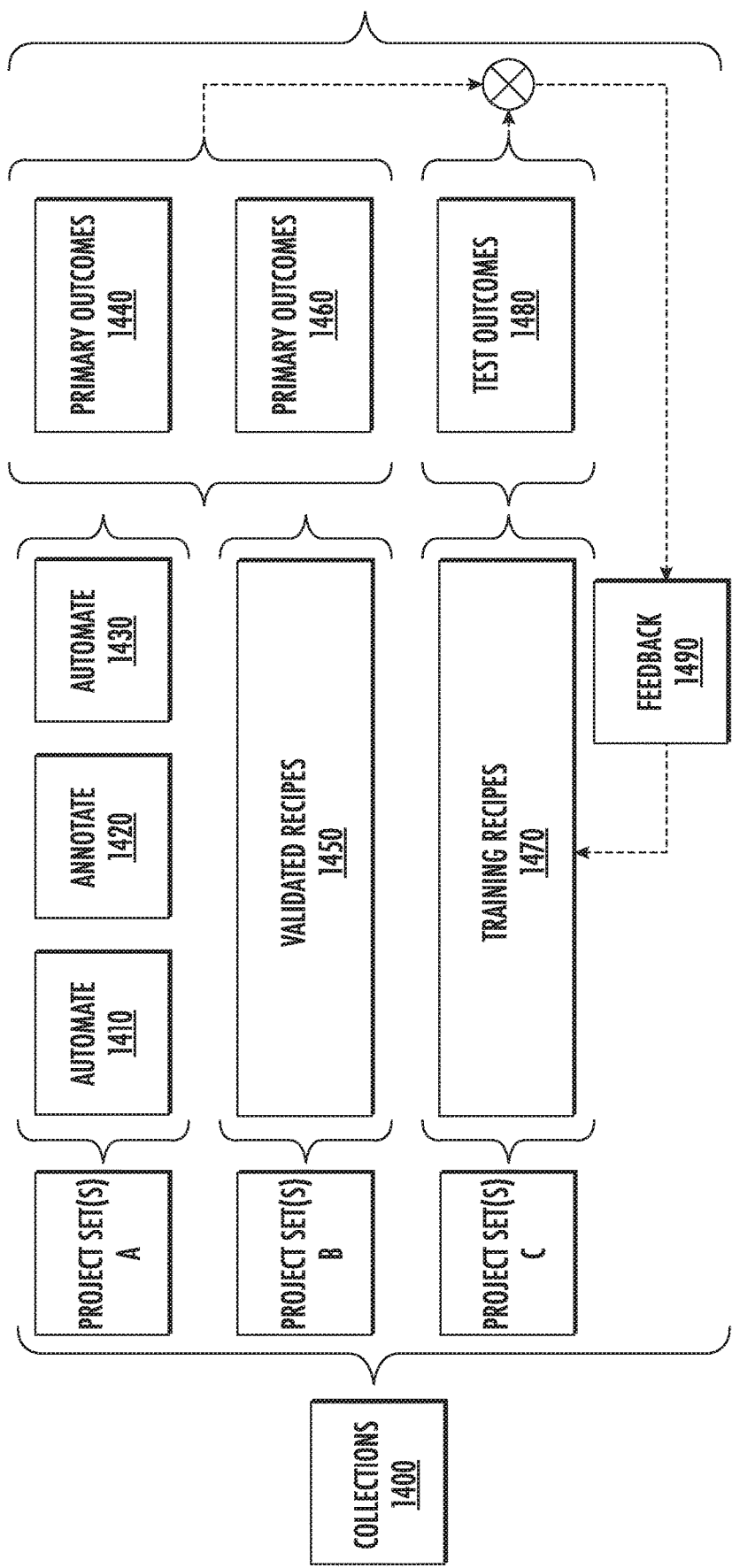
FIG. 14 is a block diagram illustrating parallel workflows in accordance with some embodiments of the present inventive concept.

In some embodiments of the present inventive concept, data Collections and Projects may be used to invoke multiple parallel Workflows as illustrated in FIG. 14. As illustrated, data within a collection 1400 may be allocated to parallel sets of Projects, here Project Sets A, B, and C. In these embodiments, Project Sets A are one or more Workflows that require user interactions to Annotate images. As illustrated, an automated step 1410 is used to present data to the user, and application interface enables the user to annotate images 1420, and an automated step aggregates and analyzes the annotations 1430. There may be multiple such Projects, for example to accumulate data from multiple experts to assess reproducibility of similar annotations instructions or may be presented to different classes of experts for different annotation instructions. All this activity is managed within the DWMS, greatly simplifying workflows, and generating outcome results. We note that the Annotation workflow 1420 may be followed by additional Recipes, and in principle followed by additional user interaction Workflows, depending on the complexity of the problem address; the integrated set inputs, Actions, Recipes, and outputs is a complete Workflow and provides a primary outcome 1440.

In parallel, Project Sets B may present data to validated Recipes 1450 that automate the computation of an outcome measure without any user action. Such a parallel application of automated Recipes may generate a unique set of outputs 1460 relative to Project Sets A or may be targeting the same set of outputs for comparative purposes. The key to Project Sets B, for explanatory purpose, is that the Recipes are validated specified for use with a Protocol.

In parallel, Project Sets C may be used in the training of new Recipes 1470. The Training Recipes 1470 may generate an outcome that is compared to Primary Outcomes of Projects A and/or B, and feedback 1490 applied to improve the performance of the Training Recipes 1480.

The process of developing a new Recipe is directed at creating validated biomarkers or objective outcome measures for automated analysis, diagnosis, or autonomous decision support. The general process of algorithm, and thus Recipe, development involves training, testing, and validation. A critical requirement for validation of algorithms is testing against a previous un-examined validation data set drawn from the target population of data.

In some embodiments of the present inventive concept, the DWMS controls allocation of data to Training sets, testing sets, and validation sets. The Diagram of FIG. 14 may be extended to Project Sets D and E, where Project Sets D are for Testing, and Sets E for Validation. A Workflow for developing a Recipe may be defined independently or in parallel with a currently accepted Workflow, allowing a user to move from a Testing Set when Training is deemed successful, and to a Validation Set when Testing is deemed to verify the Training.

In some embodiments of the present inventive concept, the DWMS automatically allocates data into these developmental test sets, and sets aside a validation set that the user and Recipe cannot access prior to the validation step. Access to the data allocations is preserved as an audit trail in the Transactions and Traceability layer of the DWMS. Once a Recipe is validated, it may be locked and escrowed for re-use.

This process may be used retrospectively on data drawn from the DWMS. New questions may be asked, Collections created, and new Projects created with new or modified Workflows, Recipes, and algorithms. Following the Recipe development process, new analysis methods, and biomarkers may be analyzed, developed, and validated.

A critical aspect of retrospect data analysis is management of owner rights and protection of human subject privacy. The License and Permission layer of the DWMS provides the keys to data allocation, where data is broadly defined as subject data, and any workflow, recipe, and algorithm libraries that may be invoked for a retrospective study.

Figure 15:
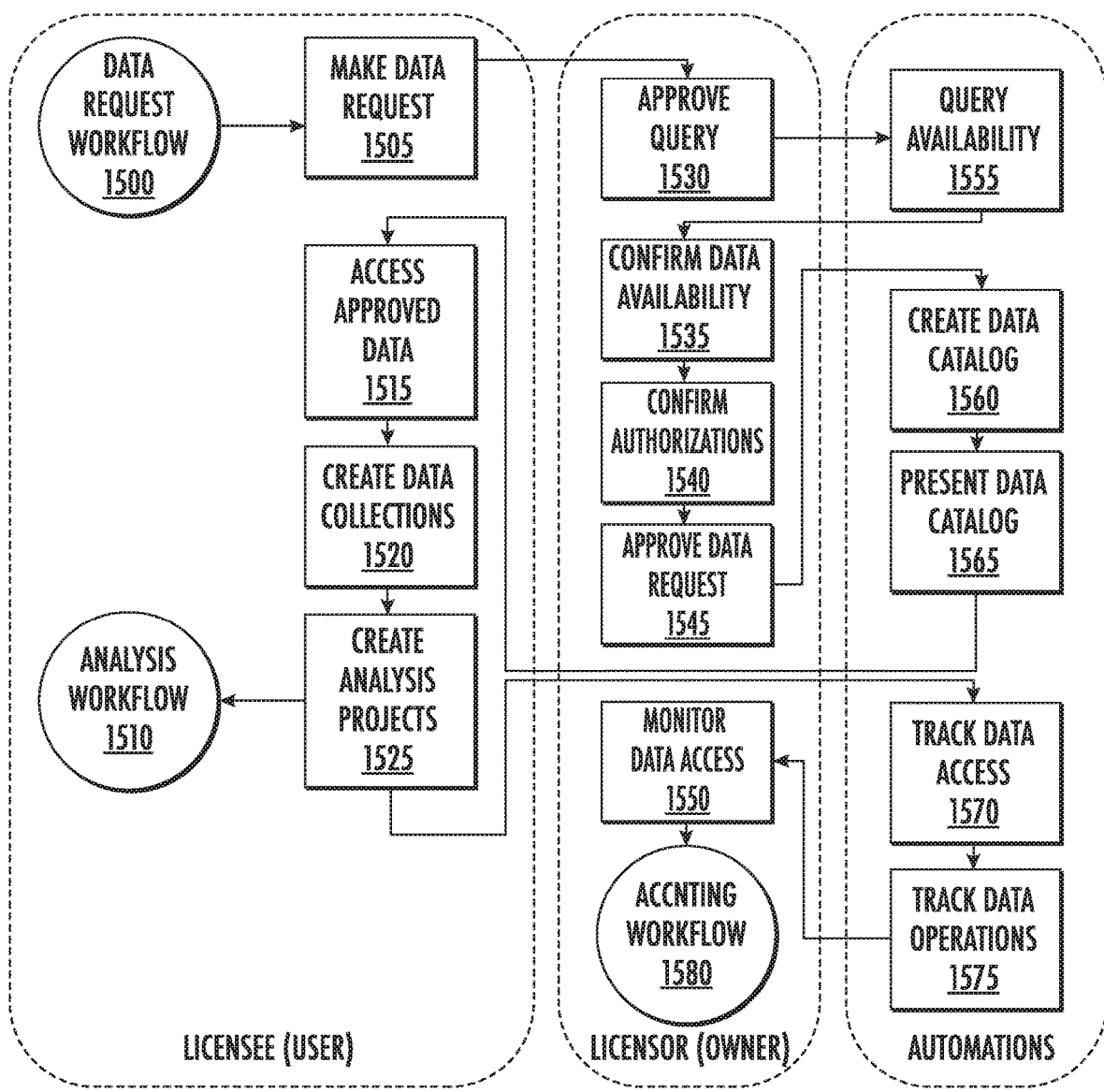
FIG. 15 is a block diagram illustrating a data request workflow in accordance with some embodiments of the present inventive concept.

In some embodiments of the present inventive concept, the DWMS includes a Data Request Workflow 1500 as shown in FIG. 15. A prospective data User (Licensee) makes a request 1505 through a DWMS query for data that meets study criteria. A DWMS administrator, data owner (Licensor), or workflow automation, approves the query 1530 based on permissions within the License and Permissions layer. The Licensor may confirm data availability 1555/1535, confirm authorizations 1540 to access data, and approve the data request 1545. An automated Recipe may then create a data catalog 1560 specific to the request and present the catalog 1565 to the Licensee. The Licensee having access to approve data 1515 may then be in control of a study, create Collections 1520 from the Catalog, and proceed with analysis Workflows 1510 as previously described (create analysis projects 1525).

The DWMS may use automations to track data access 1570 and data operations 1575 of the Licensee to monitor data access 1550. The Licensor may then engage an accounting workflow 1580 to visualize data access, ensure compliance to terms of a license, or perform traditional accounting functions such as invoicing.

In some embodiments of the present inventive concept, aggregation of analyses from experts and algorithms may be automated according a prescription in the Protocol. In some embodiments, the diagnostic interpretation of the analysis may be automated.

In some embodiments of the inventive concept, allocation of data to a library of algorithmic tests that may be used for comparative research outside of the prescribed tests associated with the Protocol may be automated.

In some embodiments of the present inventive concept, the recordation of analyses in the Transaction logs associated with data (and therefore traceable by all dimensions within the data structure) may be automated.

The Allocation of data occurs in the Data Utilization Layer for presentation to the Data Analysis layer. Prospective Data Allocations are those allocations that are mandated by the Protocol study plan. Best practice in any prospective research plan, and particularly any prospective translational medicine research plan, is to have a fully defined hypothesis, data processing plan, statistical plan, and hypothesis success metric. This plan must be prepared in advance of designing the trial or analyzing any results to avoid interpretation bias. The data allocation strategies and processing steps must be fully reproducible, and intentionally revisable to test replicability and sensitivity to input and workflow conditions. In some embodiments of the present inventive concept, the processing Recipes may be developed as a library within a Workflow Layer that drives a study. A Recipe may consist of a sequence of steps, some of which are fully automated, some of which are triggered by a User of the system, some of which require Expert interaction, and some of which are full autonomous.

For example, a Recipe to test a pharmacological intervention to reduce retinal edema may be attached to a Protocol that specifies two Exams: an OCT exam with an outcome measure of macular thickness (structural) and a visual acuity test (Subjective Function). The Encounters are scheduled and tracked using Lattice, the Exam data is collected, validated, and transferred to the Repository using the mobile communication vehicle, Local Temporary Storage, PHI removal engine and data quality assessment engine at the Validation processor, and distributed to the Repository. A Recipe is invoked with the following steps: (1) Create Collections of input data according to predefined filters, for example, separate genders, age groups, underlying health conditions into collections; (2) Assign data within Collections to Projects; and (3) Assign Projects to one or more processing paths, where processing may a new Recipe that itself is a Sequence of steps, where such steps may include expert interpretation, annotation, or labeling, automated computation, visualization and correction, automated generation of quantitative metrics from the corrected results, generation of graphical outputs, generation of tabulated outputs, and generation of an integrated report, as one example. Projects in this context may be used to manage blinded processing of data along parallel paths for statistical purposes and comparative purposes. Projects, as defined herein, contain similar data sets, though they may include randomized subsets of collections. Collections are used to manage data sets to answer distinct questions, such as impact of gender, age, intervention, etc.

In some embodiments of the present inventive concept, the data elements may include medical health information and medical images and the workflows may be associated to medical research, clinical trials, clinical diagnostics, or surgical interventions. These data elements may be specific to a specific discipline, such as ophthalmology, may be specific to a specific disease, such as glaucoma, or may be specific to a specific organ, such as an eye.

However, the data elements may be more broadly applied within a more universal data architecture that includes metadata and a joined metadata ontology, or library of terms, images of any type and a joined image ontology, other quantitative objective data, subjective data, workflows, data allocation engines, licensing and permission modules, transactional ledgers, recipes, and algorithms, all of which may be applied to the development and application of image based autonomous decision making and autonomous decision support. Applications for such a DWMS outside of medicine include, but are not limited to, autonomous vehicles, robotics, and security.

Figure 16:
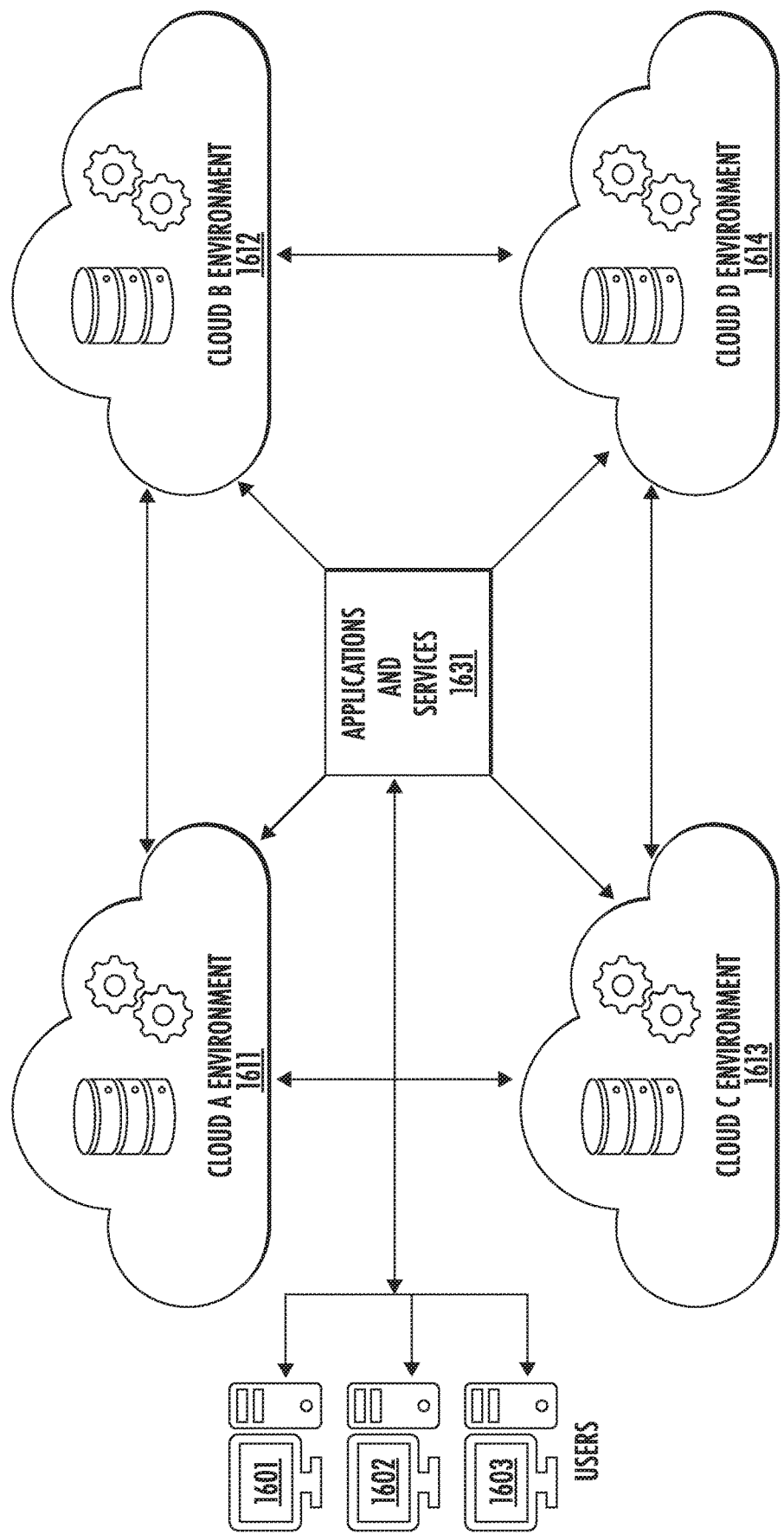
FIG. 16 is a block diagram illustrating various types of "management" in accordance with some embodiments of the present inventive concept.
Figure 17:
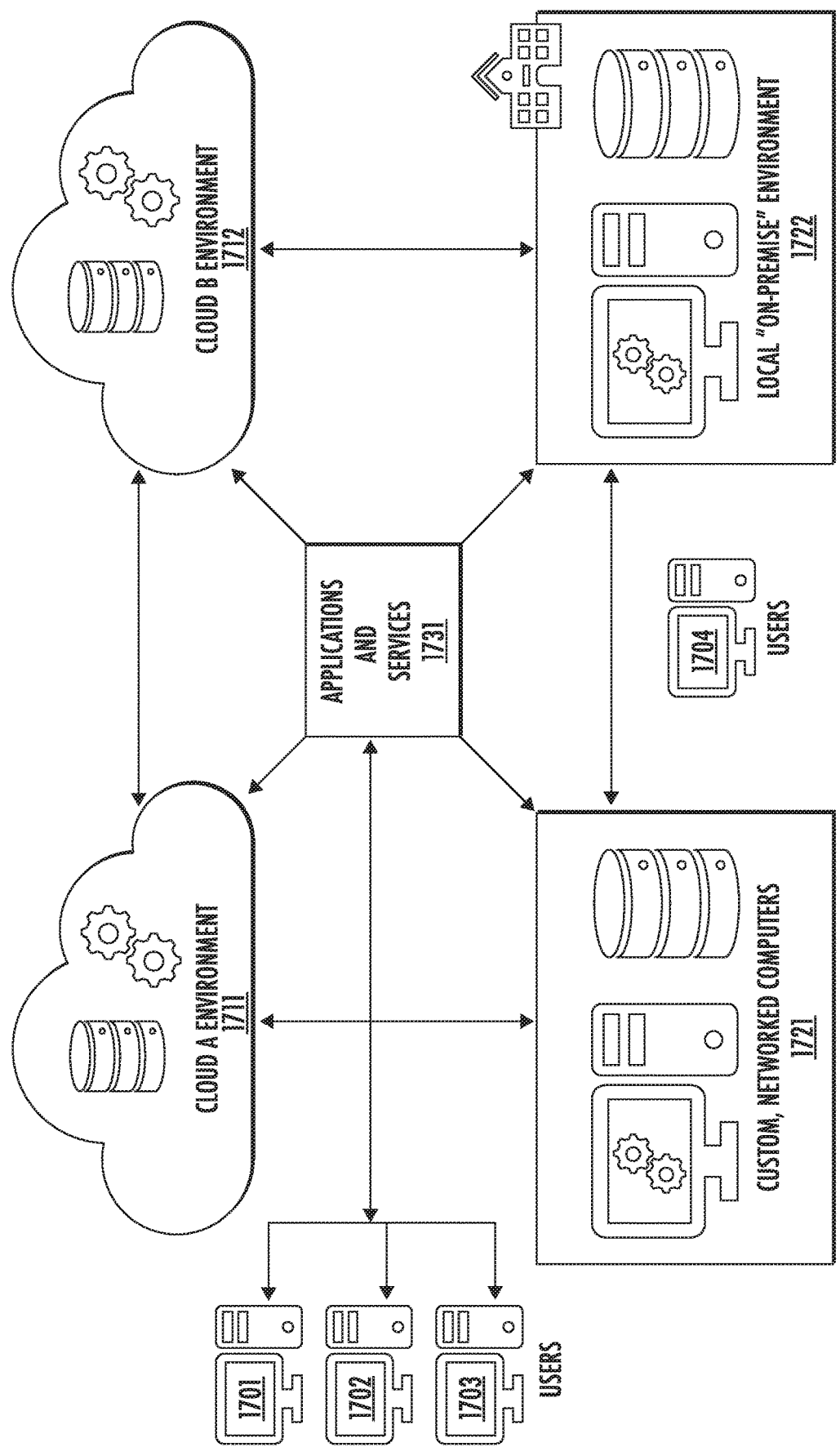
FIG. 17 is a block diagram of a system including a plurality of users, a plurality of cloud environments coupled by applications and services in accordance with some embodiments of the present inventive concept.

In some embodiments of the present inventive concept, the digital infrastructure provides both logical and physical separation of data, data processing, data transfer, and associated processing resources needed to run, install, and administer previously mentioned applications and services across a number of public cloud, private cloud, and/or local "on-premise" environments. These infrastructure capabilities allow the present inventive concept to be deployed in "multi-cloud" environments as illustrated, for example, in FIG. 16. As illustrated in FIG. 16, the multi-cloud environment provides an environment where digital infrastructure and computing is shared between multiple networked public and private cloud providers. In particular, FIG. 16 illustrates a plurality of users 1601, 1602 and 1603; a plurality of Cloud environments 1611, 1612, 1613 and 1614 all coupled through Applications and data services 1631. The infrastructure capabilities in accordance with embodiments discussed herein also allow the present inventive concept to be deployed in "hybrid-cloud" environments as illustrated in, for example, FIG. 17. As illustrated in FIG. 17, the hybrid could environment provides and environment where digital infrastructure and computing is shared between a number of networked public and private cloud providers, and local "on-premise" servers and/or computers. In particular, FIG. 17 illustrates and environment including a plurality of users 1701, 1702, 1703 and 1704; a plurality of clouds 1711 and 1712, a custom, networked environment 1721 and a local "on premise" environment couple by applications and services 1731.

Figure 18:
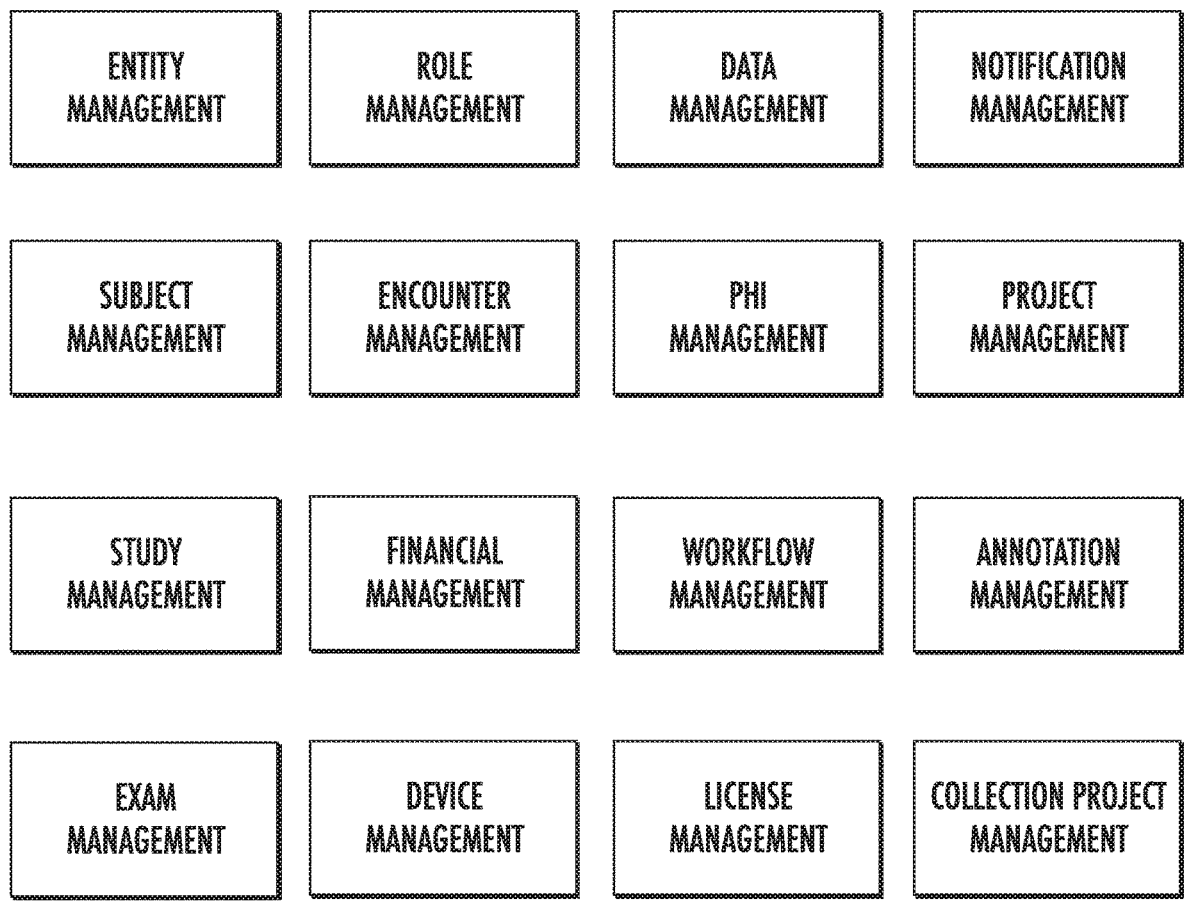
FIG. 18 is a block diagram of a system including a plurality of users, a plurality of cloud environments, custom, networked computers and a local on premise environment coupled by applications and services in accordance with some embodiments of the present inventive concept.

Referring to FIG. 18, various of the management module that may be relevant to aspects of the present inventive concept include an entity management module, a role management module, a data management module, a notification management module, a subject management module, an encounter management module, a PHI management module, a project management module, a study management module, a financial management module, a workflow management module, an annotation management module, an exam management module, a device management module, a license management module, and collection project management module. It will be understood that these management modules are provided as examples only and, therefore, this list is no exhaustive.

Figure 19:
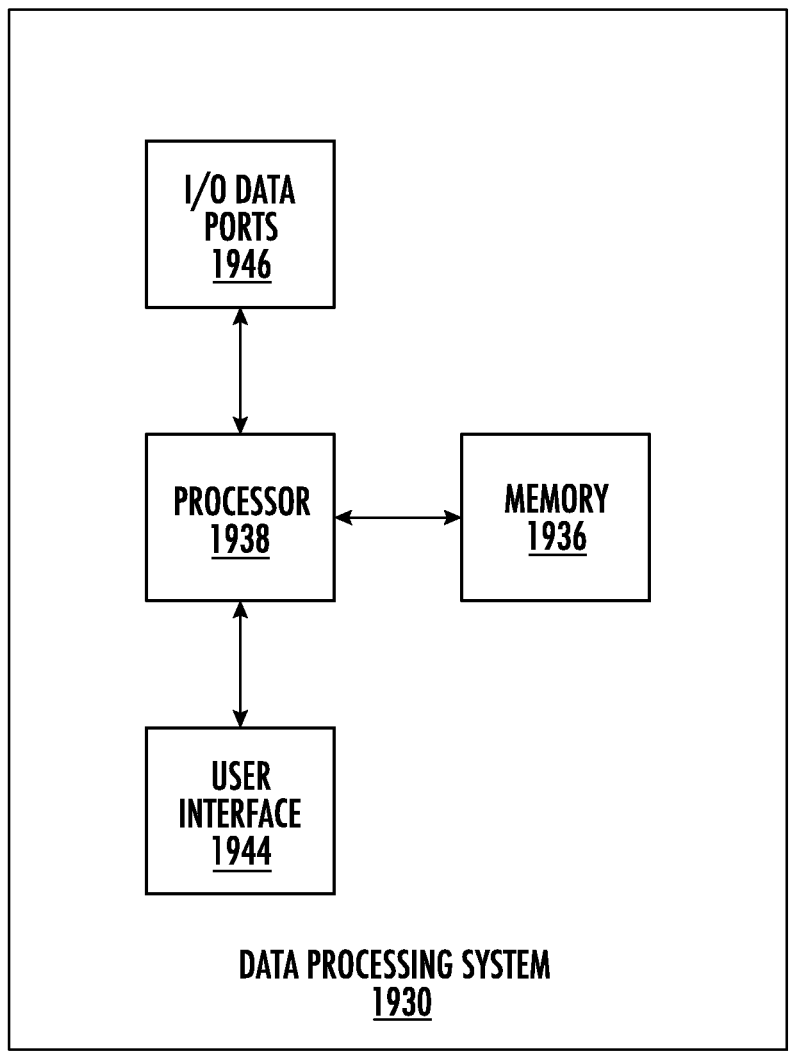
FIG. 19 is a block diagram of a data processor in accordance with some embodiments of the present inventive concept.

As is clear from the embodiments discussed above, some aspects of the present inventive concept may be implemented by a data processing system. The data processing system may be included at any module of the system without departing from the scope of the preset inventive concept. Exemplary embodiments of a data processing system 1930 configured in accordance with embodiments of the present inventive concept will be discussed with respect to FIG. 19. The data processing system 1930 may include a user interface 1944, including, for example, input device(s) such as a keyboard or keypad, a display, a speaker and/or microphone, and a memory 1936 that communicate with a processor 1938. The data processing system 1930 may further include I/O data port(s) 1946 that also communicates with the processor 1938. The I/O data ports 1946 can be used to transfer information between the data processing system 1930 and another computer system or a network using, for example, an Internet Protocol (IP) connection. These components may be conventional components such as those used in many conventional data processing systems, which may be configured to operate as described herein.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. An integrated system for collecting, storing, and distribution of images acquired of subjects in a research or clinical environment, the integrated system comprising:
   an image and data repository comprising a plurality of interoperable databases for management of structured and unstructured data;
   where the structured and unstructured data includes a plurality of images originating from one or more image-generating devices, data associated with the images, and data associated with imaged subjects;

a workflow management module in direct communication with the image and data repository and with the one or more image-generating devices and/or storage devices that store the images of the imaged subjects, the workflow management module being configured to transport the images directly from the one or more image-generating devices and/or storage devices to the image and data repository and to manage the collation and distribution of images, data associated with the raw images and the data associated with the imaged subjects in the image and data repository;

wherein the workflow management module comprises a data integration module, a data management module, a pre-processing engine and a data utilization module;

wherein the data integration module receives data from one or more user-selected electronic data sources in connection with the workflow management module; the data management module parses the data received through the data integration module into records within the image and data repository; the pre-processing engine is configured to run one or more automated algorithms on images and data prior to storing images or data in the repository; and the data utilization module distributes images and data from the repository to authorized users for analysis according to automation rules defined within the workflow management module;

wherein the automation rules include rules for masking of data for human annotation, labelling and grading and rules for parsing data into grading sets, algorithm training sets, algorithm testing sets, and algorithm validation sets;

wherein the masking and parsing of data retains traceability to the source images and data in the repository;

wherein the workflow management module further comprises automated logging to record and trace activities associated with automated processing routines applied to images and data within the framework of the workflow management module in communication with the image and data repository and automated logging to user access records for all images and data within the framework of the workflow management module in communication with the image and data repository; and wherein the ordered combination of processes and automations that comprise a specific workflow are configured by the user using a library of available operations.

2. The integrated system of claim 1, wherein the workflow management module further comprises a data analysis module configured to communicate with a plurality of internal libraries, each of the plurality of libraries being directed to metadata that travels with the images and data, ownership and permissions associated with images and data, and automation processes that apply to classes of images and data.

3. The integrated system of claim 2, wherein the plurality of libraries are constantly updated with new libraries and sub-libraries based on evolving exams and details thereof performed in a research or clinical environment.

4. The integrated system of claim 2, wherein the data analysis module comprises a plurality of separate modules directed to image and data cleaning, annotation and grading; automated image and data analysis; and analysis methods and biomarker development and validation.

5. The system of claim 2, wherein the data analysis module is configured to analyze a collection of available images and/or data provided through a data utilization module according to a recipe, wherein the recipe is configured to segregate, mask, and allocate data according to a library of rules assigned to a protocol; assemble data into a trackable collection and allocate the data for review.

6. The integrated system of claim 1, further comprising a mobile device that communicates with modules in the system, the mobile device configured to track a subject through a series of one or more image or data-generating exams; record relevant information and results during the exam; transfer the recorded information and results from the mobile device to the data analysis module and/or a storage repository, and provide a notification to one or more users that an exam has been completed and the images and data have been transferred.

7. The integrated system of claim 1, wherein the pre-processing engine is further configured to:
receive the images, data associated with the images, and data associated with imaged subjects through the workflow management module;
determine a specific set of instructions associated with the received images, data associated with the images, and data associated with imaged subjects from the workflow management module; and
process the received images, data associated with the images, and data associated with imaged subjects based on the specific set of instructions associated with the received images and data from the workflow management module;
store the processed images and data with traceability to the input images and data log the operations applied to the images and data.

8. The integrated system of claim 7, wherein the specific set of instructions associated with the received images, data associated with the images, and data associated with imaged subjects is determined by an indicator set in a data field, the indicator directing the pre-processing engine to the specific set of instructions for the received raw images, data associated with the raw images, and data associated with imaged subjects from a particular data-generating device.

9. The integrated system of claim 7, where in the pre-processing engine is further configured to at least one of validate, quantify, annotate and classify the raw images, data associated with the raw images, and data associated with imaged subjects received from the workflow management module.

10. The integrated system of claim 1, wherein the pre-processing engine is configured to:
remove non-essential or private data from the raw images, data associated with the raw images, and data associated with imaged subjects;
store the removed non-essential or private data; and
before recycling the non-essential or private data, request permission from a user associated with the raw images and data.

11. The integrated system of claim 1, wherein the workflow management module stores the images, data associated with the images, and data associated with imaged subjects in a structured manner using a relational or structured query language (SQL) database and wherein the cloud storage module stores the de-identified, processed images and data in an unstructured manner using a non-relational or Non-SQL database.

12. The integrated system of claim 1, further comprising at least one of the following modules in the cloud:
an algorithm module in communication with the cloud storage module, the algorithm module configured to apply a set of rules to at least a portion of the de-identified, processed images and data stored in the cloud storage module;

a recipe module in communicate with the cloud storage module, the recipe module configured to apply a series of algorithms to at least a portion of de-identified, processed images and data stored in the cloud storage module; and a derivation module in communication with the cloud storage module, the derivation module configured to use at least a portion of the de-identified, processed images and data stored in the cloud storage module and derive new images and data therefrom.

13. The integrated system of claim 12, wherein the derivation module is configured to assess quality of the de-identified, processed images and data; reduce noise in de-identified, processed images and data; segment the images and data; and/or measure de-identified, processed images and data.

14. The integrated system of claim 1, wherein de-identified, processed images and data stored in the cloud storage module are automatically updated by various modules in the cloud.

15. The integrated system of claim 14, wherein the modules in the cloud utilize one or more of artificial intelligence (AI), statistical abstraction; image abstraction and image extraction.

16. The integrated system of claim 1, wherein the de-identified, processed images and data stored in the cloud storage module comprise at least one of statistical data; processed images; reduced images; retrospective images; in vivo images; in vitro images; functional test results; and biospecimen test results.

17. The integrated system of claim 1, wherein transactions and operations applied to the raw images, data associated with the raw images, and data associated with imaged subjects and to subsequent processed images and data resulting from the transactions and operations are recorded in a blockchain-like ledger.

18. The integrated system of claim 17, wherein the transactions and operations recorded in the ledger include allocation of subsets of images and data used for training, testing, and validation operations.

19. A method for processing and using images acquired of subjects in a research or clinical environment, the environment including an image and data bank forming a repository comprised of a plurality of interoperable databases including a plurality of raw images originating from one or more image-generating devices, data associated with the raw images, and data associated with imaged subjects; and a workflow management module in direct communication with the image and data bank and with the one or more image-generating devices and/or storage devices that store the raw images of the imaged subjects, the workflow management module being configured to transport the raw images directly from the one or more image-generating devices and/or storage devices to the image and data bank and to manage and analyze the raw images, data associated with the raw images and the data associated with the imaged subjects in the image and data bank, wherein the workflow management module comprises a data integration module, a data management module, a pre-processing engine and a data utilization module, the method comprising:

receiving data from one or more user-selected electronic data sources in connection with the workflow management module;

parsing the data received through the data integration module into records within the image and data repository;

running one or more automated algorithms on images and data prior to storing images or data in the repository; and distributing images and data from the repository to authorized users for analysis according to automation rules defined within the workflow management module, wherein the automation rules include rules for masking of data for human annotation, labelling and grading and rules for parsing data into grading sets, algorithm training sets, algorithm testing sets, and algorithm validation sets;

wherein the masking and parsing of data retains traceability to the source images and data in the repository;

wherein the workflow management module further comprises automated logging to record and trace activities associated with automated processing routines applied to images and data within the framework of the workflow management module in communication with the image and data repository and automated logging to user access records for all images and data within the framework of the workflow management module in communication with the image and data repository; and wherein the ordered combination of processes and automations that comprise a specific workflow are configured by the user using a library of available operations.

20. A computer program product for processing and using images acquired of subjects in a research or clinical environment, the environment including an image and data bank forming a repository comprised of a plurality of interoperable databases including a plurality of raw images originating from one or more image-generating devices, data associated with the raw images, and data associated with imaged subjects; a workflow management module in direct communication with the image and data bank and with the one or more image-generating devices and/or storage devices that store the raw images of the imaged subjects, the workflow management module being configured to transport the raw images directly from the one or more image-generating devices and/or storage devices to the image and data bank and to manage and analyze the raw images, data associated with the raw images and the data associated with the imaged subjects in the image and data bank, wherein the workflow management module comprises a data integration module, a data management module, a pre-processing engine and a data utilization module, the computer program product comprising:

a non-transitory computer readable storage medium having computer readable program code embodied in said medium, the computer readable program code comprising:

computer readable program code to receive data from one or more user-selected electronic data sources in connection with the workflow management module;

computer readable program code to parse the data received through the data integration module into records within the image and data repository;

computer readable program code to run one or more automated algorithms on images and data prior to storing images or data in the repository; and computer readable program code to distribute images and data from the repository to authorized users for analysis according to automation rules defined within the workflow management module, wherein the automation rules include rules for masking of data for human annotation, labelling and grading and rules for parsing data into grading sets, algorithm training sets, algorithm testing sets, and algorithm validation sets;

wherein the masking and parsing of data retains traceability to the source images and data in the repository wherein the workflow management module further comprises automated logging to record and trace activities associated with automated processing routines applied to images and data within the framework of the workflow management module in communication with the image and data repository and automated logging to user access records for all images and data within the framework of the workflow management module in communication with the image and data repository; and wherein the ordered combination of processes and automations that comprise a specific workflow are configured by the user using a library of available operations.

* * * * *